US00RE36736E

United States Patent [19]

Davis et al.

[11] E Patent Number: Re. 36,736

[45] Reissued Date of Patent: Jun. 13, 2000

[54] SUBSTITUTED PYRROLES

[75] Inventors: Peter D. Davis, Letchworth; Christopher H. Hill, Knebworth; Geoffrey Lawton, Hitchin, all of United Kingdom

[73] Assignee: Hoffman-La Roche Inc., Nutley, N.J.

[21] Appl. No.: 09/014,198

[22] Filed: Jan. 27, 1998

Related U.S. Patent Documents

Reissue of:

[64] Patent No.: 5,057,614
Issued: Oct. 15, 1991
Appl. No.: 07/307,104
Filed: Feb. 6, 1989

[51] Int. Cl.[7] ..... C07D 209/02

[52] U.S. Cl. ..... 548/466; 548/468; 514/408; 514/414

[58] Field of Search ..... 548/466, 468; 514/408, 414

[56] References Cited

U.S. PATENT DOCUMENTS 4,107,297 8/1978 Omura et al. ..... 424/124
5,380,746 1/1995 Barth et al. .

FOREIGN PATENT DOCUMENTS 238011 3/1986 European Pat. Off. .
238011A 3/1986 European Pat. Off. .
296110 4/1988 European Pat. Off. .
296110A 4/1988 European Pat. Off. .

OTHER PUBLICATIONS

Chem. abstr., vol. 102, abstr. 6236c, p. 567, 1985.
Steglich et al., Chem. abstr., vol. 93, p. 508, abstr. 66027r, 1980.
Sarstedt et al., Chem. abstr., vol.98, p. 585, abstr. 215863t., 1983.
Chem. abstr., vol. 104, abstr. 207579g, p. 789, 1986.
Chem. abstr., vol. 101, abstr. 55460j, p. 455, 1984.

*Primary Examiner*—Deborah D. Carr
*Attorney, Agent, or Firm*—Mark E. Waddell; Bryan Cave LLP; Stephen M. Haracz

[57] ABSTRACT

Compounds of the formula

I

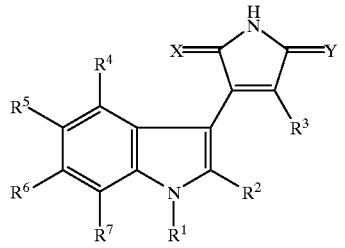

wherein $R^1$, $R^2$, $R^3$, $R^4$, $R^5$, $R^6$, $R^7$, X and Y have the signficance given in the description, are useful in the control or prevention of inflammatory, immunological, bronchopulmonary or cardiovascular disorders.

14 Claims, No Drawings

SUBSTITUTED PYRROLES

Matter enclosed in heavy brackets [ ] appears in the original patent but forms no part of this reissue specification; matter printed in italics indicates the additions made by reissue.

BRIEF SUMMARY OF THE INVENTION

The invention relates to substituted pyrroles. More particularly, the invention relates to substituted pyrroles of the formula

I

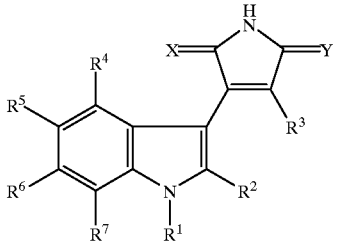

wherein $R^1$ signifies hydrogen, alkyl, aryl, aralkyl, alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula (a)

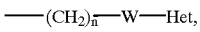

(b)

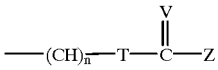

(c)

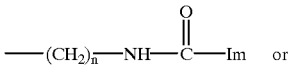

or (d)

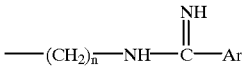

in which

Het signifies a heterocyclyl group,

W signifies NH, S or a bond,

T signifies NH or S,

V signifies O, S, NH, $NNO_2$, NCN or $CHNO_2$,

Z signifies alkylthio, amino, monoalkylamino or dialkylamino,

Im signifies 1-imidazolyl,

Ar signifies aryl, and n stands for 2–6;

$R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl;

$R^3$ signifies a carbocyclic or heterocyclic aromatic group;

$R^4$, $R^5$, $R^6$ and $R^7$ each independently signify hydrogen, halogen, alkyl, hydroxy, alkoxy, aryloxy, haloalkyl, nitro, amino, acylamino, monoalkylamino, dialkylamino, alkylthio, alkylsulphinyl or alkylsulphonyl;

and one of X and Y signifies O and the other signifies O, S, (H,OH) or (H,H);

with the proviso that $R^1$ has a significance different from hydrogen when $R^2$ signifies hydrogen, $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; as well as pharmaceutically acceptable salts of acidic compounds of formula I with bases and of basic compounds of formula I with acids.

Objects of the present invention are the compounds defined earlier per se and as therapeutically active substances; a process for their manufacture; medicaments containing said compounds and the manufacture of these medicaments; and the use of said compounds in the control or prevention of illnesses, especially of inflammatory, immunological, bronchopulmonary and cardiovascular disorders, or for the manufacture of a medicament against inflammatory, immunological, bronchopulmonary and cardiovascular disorders.

DETAILED DESCRIPTION OF THE INVENTION

The invention relates to substituted pyrroles. More particularly, the invention is concerned with substituted pyrroles of the formula

I

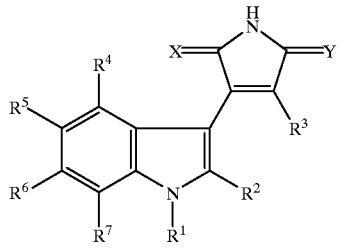

wherein $R^1$ signifies hydrogen, alkyl, aryl, aralkyl, alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula (a)

$$-(CH_2)_n-W-Het,$$

(b)

$$-(CH)_n-T-\overset{\overset{V}{\|}}{C}-Z$$

(c)

$$-(CH_2)_n-NH-\overset{\overset{O}{\|}}{C}-Im \quad \text{or}$$

(d)

$$-(CH_2)_n-NH-\overset{\overset{NH}{\|}}{C}-Ar$$

in which

Het signifies a heterocyclyl group,

W signifies NH, S or a bond,

T signifies NH or S,

V signifies O, S, NH, $NNO_2$, NCN or $CHNO_2$,

Z signifies alkylthio, amino, monoalkylamino or dialkylamino,

Im signifies 1-imidazolyl,

Ar signifies aryl, and n stands for 2–6;

$R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl;

$R^3$ signifies a carbocyclic or heterocyclic aromatic group;

$R^4$, $R^5$, $R^6$ and $R^7$ each independently signify hydrogen, halogen, alkyl, hydroxy, alkoxy, aryloxy, haloalkyl, nitro, amino, acylamino, monoalkylamino, dialkylamino, alkylthio, alkylsuphinyl or alkylsulphonyl;

and one of X and Y signifies O and the other signifies O, S, (H,OH) or (H,H);

with the proviso that $R^1$ has a significance different from hydrogen when $R^2$ signifies hydrogen $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; as well as pharmaceutically acceptable salts of acidic compounds of formula I with bases and of basic compounds of formula I with acids.

Objects of the present invention are the compounds defined earlier per se and as therapeutically active substances; a process for their manufacture; medicaments containing said compounds and the manufacture of these medicaments; and the use of said compounds in the control or prevention of illnesses, especially of inflammatory, immunological, bronchopulmonary and cardiovascular disorders, or for the manufacture of a medicament against inflammatory, immunological, bronchopulmonary and cardiovascular disorders.

As used herein, the term "alkyl", alone or in combinations, means a straight or branched-chain alkyl group containing a maximum of 7, preferably a maximum of 4, carbon atoms such as methyl, ethyl, propyl, isopropyl, butyl, sec.butyl, t-butyl and pentyl. Examples of alkoxy groups are methoxy, ethoxy, propoxy, isopropoxy, butoxy and t-butoxy. A haloalkyl group can carry one or more halogen atoms, with examples of such groups being chloromethyl and trifluoromethyl. The acyl moiety of an acylamino, acylaminoalkyl or acylthioalkyl group is derived from an alkanoic acid containing a maximum of 7, preferably a maximum of 4, carbon atoms (e.g. acetyl, propionyl or butyryl) or from an aromatic carboxylic acid (e.g. benzoyl). The term "aryl", alone or in combinations such as in arylsulphonylaminoalkyl, arylthioalkyl or aralkyl, means an unsubstituted phenyl group or a phenyl group carrying one or more, preferably one to three, substituents, examples of which are halogen, alkyl, hydroxy, benzyloxy, alkoxy, haloalkyl, nitro, amino and cyano. The term "halogen" means fluorine, chlorine, bromine or iodine.

The heterocyclic group denoted by Het can be a saturated, partially unsaturated or aromatic 5- or 6-membered heterocyclic group which can optionally carry a fused benzene ring and which can be unsubstituted or substituted, for example with one or more substituents selected from halogen, alkyl, hydroxy, alkoxy, haloalkyl, nitro, amino, acylamino, monoalkylamino, dialkylamino, alkylthio, alkylsulphinyl and alkylsulphonyl or, when the heterocyclyl group is an aromatic nitrogen-containing heterocyclic group, the nitrogen atom can carry an oxide group. Examples of such heterocyclyl groups are imidazolyl, imidazolinyl, thiazolinyl, pyridyl and pyrimidinyl.

The carbocyclic aromatic group denoted by $R^3$ can be a monocyclic or polycyclic group, preferably a monocyclic or bicyclic group, i.e. phenyl or naphthyl, which can be unsubstituted or substituted, for example with one or more, preferably one to three, substituents selected from halogen, alkyl, hydroxy, alkoxy, haloalkyl, nitro, amino, acylamino, monoalkylamino, dialkylamino, alkylthio, alkylsulphinyl and alkylsulphonyl. Examples of carbocyclic aromatic groups denoted by $R^3$ are phenyl, 2-, 3- or 4-chlorophenyl, 3-bromophenyl, 2- or 3-methylphenyl, 2,5-dimethylphenyl, 4-methoxyphenyl, 2- or 3-trifluoromethylphenyl, 2-, 3- or 4-nitrophenyl, 3- or 4-aminophenyl, 4-methylthiophenyl, 4-methylsulphinylphenyl, 4-methylsulphonylphenyl and 1- or 2-naphthyl.

The heterocyclic aromatic group denoted by $R^3$ can be a 5- or 6-membered heterocyclic aromatic group which can optionally carry a fused benzene ring and which can be unsubstituted or substituted, for example with one or more, preferably one to three, substituents selected from halogen, alkyl, hydroxy, alkoxy, haloalkyl, nitro, amino, acylamino, mono- or dialkylamino, alkylthio, alkylsulphinyl and alkylsulphonyl or, when the heterocyclic aromatic group is 3-indolyl, this can be a group of the formula (I)

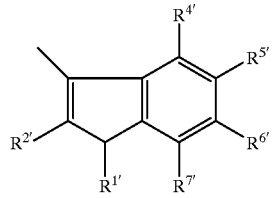

wherein $R^{1'}$, $R^{2'}$, $R^{4'}$, $R^{5'}$, $R^{6'}$ and $R^{7'}$ have any of the values accorded to $R^1$, $R^2$, $R^4$, $R^5$, $R^6$ and $R^7$ in formula I.

Examples of heterocyclic aromatic groups denoted by $R^3$ are 2- or 3-thienyl, 3-benzothienyl, 1-methyl-2-pyrrolyl, 1-benzimidazolyl, 3-indolyl, 1- or 2-methyl-3-indolyl, 1-methoxymethyl-3-indolyl, 1-(1-methoxyethyl)-3-indolyl, 1-(2-hydroxypropyl)-3-indolyl, 1-(4-hydroxybutyl)-3-indolyl, 1-[1-(2-hydroxyethylthio)ethyl]-3-indolyl, 1-[1-(2-mercaptoethylthio)ethyl]-3-indolyl, 1-(1-phenylthioethyl)-3-indolyl, 1-[1-(carboxymethylthio)ethyl]-3-indolyl and 1-benzyl-3-indolyl.

In formula I above $R^1$ preferably signifies alkyl, aminoalkyl, isothiocyanatoalkyl or a group of formula (b) in which T signifies S, V signifies NH and Z signifies amino or in which T signifies NH, V signifies NH or $NNO_2$ and Z signifies amino. In an especially preferred embodiment, $R^1$ signifies methyl, 3-aminopropyl, 3-isothiocyanatopropyl or a just-mentioned group of formula (b) in which n stands for 3. Preferably, $R^2$ signifies hydrogen. $R^3$ preferably signifies phenyl which is monosubstituted by halogen, especially chlorine or bromine, alkyl, especially methyl, alkoxy, especially methoxy, haloalkyl, especially trifluoromethyl, nitro, amino, alkylthio, especially methylthio, alkylsulphinyl, especially methylsulphinyl, or alkylsulphonyl, especially methylsulphonyl, or a group of formula (i) hereinbefore, especially one in which $R^{1'}$ signifies methyl, methoxymethyl, 1-methoxyethyl, 2-hydroxypropyl, 4-hydroxybutyl, 1-(2-hydroxyethylthio)ethyl, 1-(2-mercaptoethylthio)ethyl, 1-phenylthioethyl or 1-(carboxymethylthio)ethyl, particularly methyl, and $R^{2'}$, $R^{4'}$, $R^{5'}$, $R^{6'}$ and $R^{7'}$ each signify hydrogen. Preferably, $R^4$, $R^5$, $R^6$ and $R^7$ each signify hydrogen.

It will thus be evident that especially preferred compounds of formula I are those in which $R^1$ signifies methyl, 3-aminopropyl, 3-isothiocyanatopropyl or a group of formula (b) in which T signifies S, V signifies NH, Z signifies amino and n stands for 3 or in which T signifies NH, V signifies NH or $NNO_2$, Z signifies amino and n stands for 3, $R^2$ signifies hydrogen, $R^3$ signifies phenyl which is monosubstituted by chlorine, bromine, methyl, methoxy, trifluoromethyl, nitro, amino, methylsulphinyl or methylsulphonyl or a group of formula (i) above in which $R^{1'}$ signifies methyl and $R^{2'}$, $R^{4'}$, $R^{5'}$, $R^{6'}$ and $R^{7'}$ each signify hydrogen and $R^4$, $R^5$, $R^6$ and $R^7$ each signify hydrogen.

Particularly preferred compounds of formula I above are:

3-(2-Chlorophenyl)-4-(1-methyl-3-indolyl)-1H-pyrrole-2,5-dione, 3-(1-methyl-3-indolyl)-4-(2-nitrophenyl)-1H-pyrrole-2,5-dione, 3,4-bis(1-methyl-3-indolyl)-1H-pyrrole-2,5-dione and 3-[1-(3-aminopropyl)-3-indolyl]-4-(1-methyl-3-indolyl)-1H-pyrrole-2,5-dione, 3-[1-[3-(amidinothio)propyl]-3-indolyl]-4-(1-methyl-3-indolyl)-1H-pyrrole-2,5-dione, 3-(1-methyl-3-indolyl)-4-[1-[3-(2-nitroguanidino)propyl]-3-indolyl]-1H-pyrrole-2,5-dione and 3-[1-(3-isothiocyanatopropyl)-3-indolyl]-4-(1-methyl-3-indolyl)-1H-pyrrole-2,5-dione.

The compounds of formula I as well as pharmaceutically acceptable salts of acidic compounds of formula I with bases and of basic compounds of formula I with acids are manufactured in accordance with the invention by (a) for the manufacture of a compound of formula I in which X and Y both signify O, reacting a compound of the general formula

II

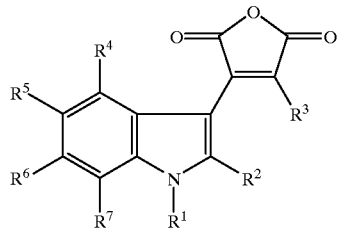

wherein $R^1$, $R^2$, $R^3$, $R^4$, $R^5$, $R^6$ and $R^7$ have the significance given earlier, with ammonia under pressure or with hexamethyldisilazane and methanol, or (b) for the manufacture of a compound of formula I in which $R^1$ signifies hydrogen and X and Y both signify O, reacting a compound of the general formula

III

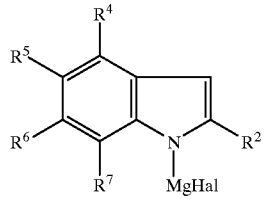

wherein $R^2$, $R^4$, $R^5$, $R^6$ and $R^7$ have the significance given earlier and Hal signifies halogen, with a compound of the general formula

IV

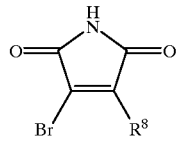

wherein $R^8$ has the same significance as $R^3$ hereinbefore or represents bromine, or (c) for the manufacture of a compound of formula I in which $R^3$ signifies 1-benzimidazolyl and X and Y both signify O, reacting a compound of the general formula

V

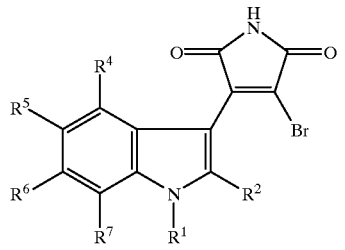

wherein $R^1$, $R^2$, $R^4$, $R^5$, $R^6$ and $R^7$ have the significance given earlier, with an alkali metal derivative of benzimidazole, or (d) for the manufacture of a compound of formula I in which one of X and Y signifies O and the other signifies S, reacting a compound of formula I in which X and Y both signify O with a sulphurizing agent, or (e) for the manufacture of a compound of formula I in which one of X and Y signifies O and the other signifies (H,OH), reducing a compound of formula I in which X and Y both signify O with a complex metal hydride, or (f) for the manufacture of a compound of formula I in which one of X and Y signifies O and the other signifies (H,H), catalytically hydrogenating a compound of formula I in which one of X and Y signifies O and the other signifies (H,OH), or (g) for the manufacture of a compound of formula I in which $R^1$ signifies alkyl, aralkyl, alkoxyalkyl or hydroxyalkyl, appropriately N-substituting a compound of formula I in which $R^1$ signifies hydrogen, and (h) if desired, functionally modifying a reactive substituent present in a compound of formula I obtained, and (i) also if desired, converting an acidic compound of formula I into a pharmaceutically acceptable salt with a base or converting a basic compound of formula I into a pharmaceutically acceptable salt with an acid.

The reaction of a compound of formula II with ammonia under pressure in accordance with embodiment (a) of the process is conveniently carried out using aqueous ammonia (preferably 33% aqueous ammonia) and in the presence of a water-miscible inert organic solvent such as dimethylformamide (DMF) or the like. The reaction is preferably carried out at an elevated temperature, for example a temperature in the range of about 100° to 150° C. In general, the reaction is completed within about 0.5 to 5 hours.

The reaction of a compound of formula II with hexamethyldisilazane and methanol, also in accordance with embodiment (a) of the process, is conveniently carried out in an inert organic solvent such as a halogenated hydrocarbon (e.g. chloroform, carbon tetrachloride or chlorobenzene) or an aromatic hydrocarbon (e.g. benzene, toluene or a xylene) and at an elevated temperature (e.g. a temperature between about 40° and 110° C.).

The reaction of a compound of formula III with a compound of formula IV in accordance with embodiment (b) of the process can be carried out in a manner known per se for Grignard reactions; for example, in an inert organic solvent, e.g. one of the above cited aromatic hydrocarbons, and at a temperature between about room temperature and the reflux temperature of the reaction mixture. In general, the reaction takes from several hours (e.g. 18 hours) to a few days (e.g. 5 days). The compounds of formula III are expediently prepared in situ from indole or an appropriately substituted indole and a suitable alkylmagnesium halide such as methylmagnesium bromide or iodide, in a known manner. The symbol Hal in the compounds of formula III preferably stands for bromine or iodine. When a compound of formula III is reacted with a compound of formula IV in which $R^8$ represents bromine there is obtained a symmetrically substituted compound of formula I, i.e. a compound in which $R^3$ signifies a group of formula (i) above wherein $R^{1'}$, $R^{2'}$, $R^{4'}$, $R^{5'}$, $R^{6'}$ and $R^{7'}$ have the same significances as, respectively, $R^1$, $R^2$, $R^4$, $R^5$, $R^6$ and $R^7$ in the compound of formula III.

Conventional procedures can be used in carrying out the reaction of a compound of formula V with an alkali metal derivative of benzimidazole in accordance with embodiment (c) of the process. The reaction is conveniently carried out in an inert organic solvent such as DMF. The temperature at which the reaction is carried out is not critical, but an elevated temperature (e.g. about 45° to 95° C.) is preferred. The alkali metal, preferably sodium, derivative is preferably prepared in situ by treating benzimidazole with an appropriate alkali metal base such as an alkali metal hydride (e.g. sodium hydride).

The sulphurization in accordance with embodiment (d) of the process is conveniently carried out using phosphorus pentasulphide, Lawesson's reagent [2,4-bis(4-methoxyphenyl)-1,2-dithioxo-1,3,2,4-dithiaphosphetane; Bull. Soc. Chim. Belg. 87 (1978) 229–238] or Davy reagent [2,4-bis(methylthio)-1,3,2,4-dithiadiphosphetane; Sulfur Lett. 1983, 1, 167]. This reaction is expediently carried out in an inert organic solvent such as an aliphatic or cyclic ether (e.g. dimethoxyethane) or an aromatic hydrocarbon which may be halogenated (e.g. benzene, toluene or chlorobenzene) and at an elevated temperature, especially at the reflux temperature of the reaction mixture.

The reduction in accordance with embodiment (e) of the process can be carried out in a manner known per se. An alkali metal aluminium hydride such as lithium aluminium hydride is preferably used as the complex metal hydride, although other hydrides such as diisobutylaluminium hydride and sodium dihydro-bis(2-methoxyethoxy) aluminate can also be used. Suitable inert organic solvents in which this reduction can be carried out include aliphatic and cyclic ethers such as diethyl ether or tetrahydrofuran (THF) and hydrocarbons such as hexane, benzene and toluene. Conveniently, this reduction is carried out at about room temperature.

Conventional procedures can be used in carrying out the catalytic hydrogenation in accordance with embodiment (f) of the process. Thus, the catalytic hydrogenation can be carried out in the presence of a noble metal catalyst such as a palladium or platinum catalyst, e.g. palladium/carbon (Pd/C),) and an inert organic solvent such as an alkanol (e.g. methanol or ethanol). This catalytic hydrogenation is expediently carried out at about room temperature and under atmospheric pressure.

The N-substitution of a compound of formula I in which $R^1$ signifies hydrogen in accordance with embodiment (g) of the process can be carried out according to known methods for the $N^1$-substitution of indoles. For example, a hydroxyalkyl group $R^1$ can be introduced into a compound of formula I in which $R^1$ signifies hydrogen by firstly converting said compound into an alkali metal derivative (e.g. sodium derivative), for example using an alkali metal hydride (e.g. sodium hydride), and then treating this derivative with an agent yielding a hydroxyalkyl group (e.g. an alkylene oxide such as propylene oxide). Again, for example, an alkoxyalkyl group $R^1$ can be introduced by treating a compound of formula I in which $R^1$ signifies hydrogen with an appropriate aldehyde dialkyl acetal in the presence of an acid (e.g. p-toluenesulphonic acid) at an elevated temperature. Further, for example, a compound of formula I in which $R^1$ signifies hydrogen can be reacted with an alkyl or aralkyl halide in the presence of a base to give a compound of formula I in which $R^1$ signifies alkyl or aralkyl.

A reactive substituent present in a compound of formula I can be functionally modified, if desired, in accordance with embodiment (h) of the process. All of modifications can be carried out according to methods known per se. For example, a nitro group can be reduced to an amino group and the latter can be appropriately alkylated or acylated. Likewise, an aminoalkyl group can be appropriately alkylated, acylated or sulphonylated. Again, for example, an alkylthio group or an alkylthioalkyl group can be oxidized to an alkylsulphinyl or alkylsulphinylalkyl group, respectively and the latter can be oxidized further to an alkylsulphonyl or alkylsulphonylalkyl group, respectively. An alkoxycarbonylalkyl group can be saponified to a carboxyalkyl group and the latter can be appropriately amidated or esterified. An alkoxyalkyl group can be converted into an alkylthioalkyl or arylthioalkyl group by means of an appropriate alkanethiol or thiophenol. An azidoalkyl group can be converted by catalytic hydrogenation into an aminoalkyl group and the latter can be subjected to a number of modifications. For example, the aminoalkyl group can be converted using 1,1'-thiocarbonyldiimidazole into an isothiocyanatoalkyl group. Again, for example, an aminoalkyl group containing 2–6 carbon atoms in the alkyl moiety can be converted into a group of formula (a) hereinbefore in which W signifies NH by reaction with a reactive derivative of an appropriate heterocyclic compound or into a group of formula (b) hereinbefore in which (i) T signifies NH, V signifies NH and Z signifies amino using 3,5-dimethylpyrazole-1-carboxamidine, (ii) T signifies NH, V signifies $NNO_2$ and Z signifies amino using 3,5-dimethyl-$N^2$-nitro-1-pyrazole-1-carboxamide, (iii) T signifies NH, V signifies NCN and Z signifies alkylthio using a dialkyl N-cyanodithioiminocarbonate or (iv) T signifies NH, V signifies $CHNO_2$ and Z signifies alkylthio using a 1,1-bis (alkylthio)-2-nitroethylene. Yet again, for example, an aminoalkyl group containing 2–6 carbon atoms in the alkyl moiety can be converted into a group of formula (c) hereinbefore by reaction with 1,1'-carbonyldiimidazole or into a group of formula (d) hereinbefore by reaction with an appropriate benzimidate. The conversion of a group of formula (b) in which T signifies NH, V signifies NCN or $CHNO_2$ and Z signifies alkylthio into a corresponding group of formula (b) in which Z signifies amino or mono- or dialkylamino can be effected by means of ammonia or a mono- or a dialkyamine, respectively. An isothiocyanatoalkyl group can be converted into a group of formula (b) in which T signifies NH, V signifies S and Z signifies amino by treatment with ammonia. An alkylcarbonyloxyalkyl group can be saponified to a hydroxyalkyl group and the latter can be converted in a known manner into a haloalkyl group or into an alkylsulphonyloxyalkyl group. A hydroxyalkyl group can also be converted into an aminoalkylaminoalkyl group by treatment with trifluoromethanesulphonic anhydride followed by reaction with an appropriate diaminoalkane. A hydroxyalkyl group containing 2–6 carbon atoms in the alkyl moiety can be treated firstly with trifluoromethanesulphonic anhydride and then with an appropriate heterocyclic compound (e.g. pyridine) to obtain a group of formula (a) in which W signifies a bond. An alkylsulphonyloxyalkyl group can be subjected to a number of conversions, for example it can be converted into a mono-, di- or trialkylaminoalkyl group by means of a mono-, di- or a trialkylamine, respectively; into a cyanoalkyl group using an alkali metal cyanide, into an alkylthioalkyl group using an alkali metal alkanethiolate or into an acylthioalkyl group using an alkali metal thiolacylate. An alkylsulphonyloxy ($C_2$–$C_6$-alkyl) group can also be converted by means of thiourea into a group of formula (b) hereinbefore in which T signifies S, V signifies NH and Z signifies amino using thiourea. The conversion of a cyanoalkyl group into an amidinoalkyl group by means of ammonia, the conversion of an acylthioalkyl group into a mercaptoalkyl group by treatment with aqueous ammonia as well as the conversion of a benzyloxy-substituted aryl group into a hydroxy-substituted aryl group by hydrogenolysis can be mentioned as further examples of substituent modifications which can be carried out. Further, a group of formula (c) can be converted into a group of formula (b) in which T signifies NH, V signifies O and Z signifies amino using alcoholic ammonia. It will be appreciated that the foregoing modifications are given by way of example only and that other modifications within the purview of a person skilled in the art are also possible.

The conversion of an acidic compound of formula I into a pharmaceutically acceptable salt in accordance with embodiment (i) of the process can be carried out by treatment with a suitable base in a manner known per se. Suitable salts are those derived not only from inorganic bases, e.g. sodium, potassium or calcium salts, but also from organic bases such as ethylenediamine, monoethanolamine or diethanolamine. The conversion of a basic compound of formula I into a pharmaceutically acceptable salt can be carried out by treatment with a suitable acid in a manner known per se. Suitable salts are those derived not only from inorganic acids e.g. hydrochlorides, hydrobromides, phosphates or sulphates, but also from organic acids, e.g. acetates, citrates, fumarates, tartrates, maleates, methanesulphonates or p-toluenesulphonates.

The starting materials of formula II can be prepared by reacting a compound of the general formula

VI

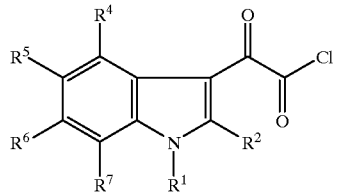

with a compound of the general formula $$HOOC—CH_2—R^3 \qquad \text{VII}$$

wherein $R^1$ to $R^7$ have the significance given earlier, and, if desired, functionally modifying a reactive substituent present in an obtained compound of formula II, in the same manner as described earlier in connection with the functional modification of a reactive substituent present in a compound of formula I.

The reaction of a compound of formula VI with a compound of formula VII is preferably carried out in the presence of an acid-binding agent, expediently a tertiary amine such as a trialkylamine (e.g. triethylamine or diisopropylethylamine), and in an inert organic solvent such as a halogenated aliphatic hydrocarbon.

The compounds of formula VI can be prepared by reacting a compound of the general formula

VIII

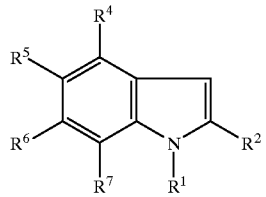

wherein $R^1$ to $R^7$ have the significance given earlier, with oxalyl chloride, conveniently in an inert organic solvent such as a halogenated aliphatic hydrocarbon, at a temperature from about 0° C. to the reflux temperature of the solvent. The resulting compound of formula VI can be reacted in situ with that of formula VII or can be isolated and purified prior to the reaction with the compound of formula VII.

As mentioned earlier, the compounds of formula III are expediently prepared from indole or an appropriately substituted indole, i.e. from a compound of formula VIII in which $R^1$ is hydrogen, and a suitable alkylmagnesium halide such as methylmagnesium bromide or iodide in a known manner, for example by treating a solution of the compound of formula VIII in an inert organic solvent such as an aromatic hydrocarbon with an ethereal solution of the alkylmagnesium halide at about room temperature.

The compounds of formula IV in which $R^8$ has the same significance as $R^3$ hereinbefore can be prepared by brominating a compound of the general formula

IX

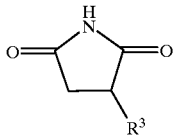

wherein $R^3$ has the significance given earlier.

The compounds of formula V (or those of formula IV wherein $R^8$ is a group of formula (i) above) can be prepared by reacting a compound of formula III above with dibromomaleimide, i.e. the compound of formula IV, wherein $R^8$ is bromine.

The bromination of a compound of formula IX can be carried out conveniently using elemental bromine in the presence or absence of an inert organic solvent, e.g. an aliphatic ether. The bromination is preferably carried out at an elevated temperature e.g. 100°–120° C. when no solvent is used and the reflux temperature of the mixture when a solvent is used.

The reaction of a compound of formula III with dibromomaleimide can be carried out in a manner analogous to that described earlier in connection with embodiment (b) of the process.

The pyrroles of formula I and their pharmaceutically acceptable salts are protein kinase inhibitors; they inhibit cellular processes, for example cell proliferation, and can be used in the control or prevention of illnesses, e.g. of inflammatory disorders such as arthritis, immune diseases, in conjunction with organ transplants and also in oncology. They inhibit infection of cells with human immunodeficiency virus and are thus useful in the treatment of AIDS. They also inhibit smooth muscle contraction and can therefore be used against cardiovascular and bronchopulmonary disorders. Further, they are also useful in asthma therapy.

The activity of the present compounds in inhibiting protein kinase C can be demonstrated by means of the in vitro assay system described e.g. in BBRC 19 (1979) 1218.

The $IC_{50}$ figures in the following Table, represent that concentration of test compound which reduces by 50% the protein kinase-induced incorporation of $^{32}P$ from [$\gamma$-$^{32}P$] ATP into histone.

TABLE

| Compound | $IC_{50}$ |
|---|---|
| 3-[1-(2-Carbamoylethyl)-3-indolyl]-4-(1-methyl-3-indolyl)-[H-pyrrole-2,5-dione | 0.5 $\mu$M |
| 3-(5-Amino-1-methyl-3-indolyl)-4-(1-methyl-3-indolyl)-1H-pyrrole-2,5-dione | 0.6 $\mu$M |
| 3-(1-Methyl-3-indolyl)-4-(3-(methylphenyl)-1H-pyrrole-2,5-dione | 1.0 $\mu$M |
| 3-[1-[3-(Amidinothio)propyl]-3-indolyl]-4-(1-methyl-3-indolyl)-1-H-pyrrole-2,5-dione | 0.010 $\mu$M |

TABLE-continued

| Compound | $IC_{50}$ |
|---|---|
| 3-(1-Methyl-3-indolyl)-4-[1-[3-(2-nitroguanidino)propyl]-3-indolyl]-1H-pyrrole-2,5-dione | 0.025 $\mu$M |
| 3-[1(3-Isothiocyanatopropyl)-3-indolyl]-4-(1-methyl-3-indolyl)-1H-pyrrole-2,5-dione | 0.008 $\mu$M |

The pyrroles of formula I and their aforementioned salts can be used as medicaments, e.g. in the form of pharmaceutical preparations, which can be administered orally, e.g. in the form of tablets, coated tablets, dagrees, hard or soft gelatine capsules, solutions, emulsions or suspensions. They can also be administered rectally (e.g. in the form of suppositories) or parenterally (e.g. in the form of injection solutions).

For the manufacture of pharmaceutical preparations these compounds can be formulated with therapeutically inert, inorganic or organic carriers. Lactose, maize starch or derivatives thereof, talc, steric acid or its salts can be used as such carriers for tablets, coated tablets, dagrees and hard gelatine capsules. Suitable carriers for soft gelatine capsules are vegetable oils, waxes, fats, semi-solid or liquid polyols. Depending on the nature of the active substance no carriers are, however, generally required in the case of soft gelatine capsules. Suitable carriers for the manufacture of solutions and syrups are, water, polyols, saccharose, invert sugar and glucose. Suitable carriers for injection solutions are water, alcohols, polyols, glycerine and vegetable oils. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned above, the pyrroles of formula I and their aforementioned salts can be used in the control or prevention of illnesses, especially of inflammatory, immunological, bronchopulmonary and cardiovascular disorders. The dosage can vary within wide limits and will, of course, be adjusted to the individual requirements in each particular case. In general, in the case of oral administration to adults, a daily dosage of about 5 to 500 mg should be appropriate, although the upper limit may be exceeded when this is found to be expedient. The daily dosage can be administered as a single dose or in divided doses.

The following Examples illustrate the present invention:

EXAMPLE 1

0.4 g of 3-(1-methyl-3-indolyl)-4-(1-methyl-5-nitro-3-indolyl)furan-2,5-dione was treated with 3 ml of DMF and 20 ml of 33% aqueous ammonia and heated at 140° C. for 3.5 hours. The cooled mixture was filtered and the residue was washed with water and dried to give 0.29 g of 3-(1-methyl-3-indolyl)-4-(1-methyl-5-nitro-3-indolyl)-1H-pyrrole-2,5-dione, m.p. 282°–284° C.

The furandione starting material was prepared as follows:

0.7 g of 1-methyl-5-nitroindole-3-glyoxylyl chloride in 20 ml of dichloromethane was treated with 0.85 ml of triethylamine and 0.5 g of 1-methylindol-3-yl-acetic acid. The mixture was left to stand at room temperature for 16 hours and then concentrated. The residue was chromatographed on silica gel with 50% ethyl acetate in petroleum ether to give 0.42 g of furandione, m.p. 220°–221° C.

EXAMPLE 2

56 mg of 3-(1-methyl-3-indolyl)-4-(1-naphthyl)furan-2,5-dione were treated with 5 ml of DMF and 5 ml of 33% aqueous ammonia and the mixture was heated at 130° C. for 5 hours. The formed precipitate was filtered off, washed with water and dried to give 53 mg of 3-(1-methyl-3-indolyl)-4-(1-naphthyl)-1H-pyrrole-2,5-dione, m.p. 258°–260° C.

The furandione starting material was prepared as follows:

To 1.1 g of 1-methylindole-3-glyoxylyl chloride in 30 ml of dichloromethane were added 1.65 ml of triethylamine followed by a solution of 0.93 g of 1-naphthylacetic acid in 20 ml of dichloromethane. After stirring for 16 hours the mixture was concentrated and the residue was purified on silica gel with dichloromethane to give 295 mg of furandione, m.p. 217°–219° C.

EXAMPLE 3

0.30 g of 3-(1-methyl-3-indolyl)-4-(3-methylphenyl) furan-2,5-dione was treated with 8 ml of DMF and 60 ml of 33% aqueous ammonia and heated at 150° C. for 5 hours and then allowed to cool. The formed precipitate was filtered off, washed with water and dried to give 162 mg of 3-(1-methyl-3-indolyl)-4-(3-methylphenyl)-1H-pyrrole-2,5-dione, m.p. 243° C.

The furandione starting material was prepared as follows:

1.5 g of 1-methylindole-3-glyoxylyl chloride in 30 ml of dichloromethane at 0° C. were treated with 2.17 ml of triethylamine and 1.02 g of 3-methylphenylacetic acid. The mixture was allowed to warm to room temperature and stirred overnight. Silica was added and the solvent was evaporated. The silica and adsorbed products were purified on silica gel with 20% ethyl acetate in petroleum ether to give 307 mg of furandione, m.p. 158°–160° C.

EXAMPLE 4

160 mg of 3-(1-benzothiophen-3-yl)-4-(1-methyl-3-indolyl)furan-2,5-dione were treated with 2 ml of DMF and 20 ml of 33% aqueous ammonia and the mixture was heated at 140° C. for 5 hours. The cooled mixture was filtered and the residue was washed with water and dried. The solid was purified on silica gel with 50% ethyl acetate in petroleum ether to give 20 mg of 3-(1-benzothiophen-3-yl)-4-(1-methyl-3-indolyl)-1H-pyrrole-2,5-dione, m.p. 250°–255° C.

The furandione starting material was prepared as follows:

1.0 g of 1-methylindole-3-glyoxylyl chloride in 20 ml of dichloromethane was treated with 1.6 ml of triethylamine and a solution of 0.87 g of 1-benzothiophen-3-yl-acetic acid in dichloromethane. After leaving to stand at room temperature for 16 hours the mixture was concentrated and the residue was chromatographed on silica gel with 50% ethyl acetate in hexane to give 0.33 g of furandione, m.p. 165° C.

EXAMPLE 5

0.28 g of 3-(1-methyl-3-indolyl)-4-(3-thienyl)furan-2,5-dione was treated with 10 ml of DMF and 40 ml of 33% aqueous ammonia. The mixture was heated at 140° C. for 4 hours. The cooled solution was poured into 150 ml of water and the resulting precipitate was filtered off and dried to give 0.15 g of 3-(1-methyl-3-indolyl)-4-(3-thienyl)-1H-pyrrole-2,5-dione, m.p. 211°–212° C.

The furandione starting material was prepared as follows:

1.1 g of 1-methylindole-3-glyoxylyl chloride in 10 ml of dichloromethane were treated with 1.65 ml of triethylamine and a solution of 0.71 g of 3-thiopheneacetic acid in dichloromethane. After stirring at room temperature for 2 hours the mixture was concentrated and the residue was purified on silica gel with dichloromethane to give 0.42 g of furandione, m.p. 162°–164° C.

EXAMPLE 6

0.17 g of 3-(5-amino-1-methyl-3-indolyl)-4-(1-methyl-3-indolyl)furan-2,5-dione was treated with 4 ml of DMF and 30 ml of 33% aqueous ammonia and the mixture was heated at 140° C. for 4 hours. The cooled solution was filtered and the residue was washed with water to give 0.08 g of 3-(5-amino-1-methyl-3-indolyl)-4-(1-methyl-3-indolyl)-1H-pyrrole-2,5-dione , m.p. 254°–256° C.

The furandione starting material was prepared as follows:

0.2 g of 3-(1-methyl-3-indolyl)-4-(1-methyl-5-nitro-3-indolyl)furan-2,5-dione in 50 ml of THF was hydrogenated over 0.2 g of 10% Pd/C for 23 hours. The mixture was filtered and the solvent was evaporated to give 0.17 g of furandione, m.p. 130°–134° C.

EXAMPLE 7

0.050 g of the product of Example 6 was treated with 10 ml of acetic anhydride at room temperature for 1 hour. The excess acetic anhydride was evaporated to give 0.039 g of 3-(5-acetamido-1-methyl-3-indolyl)-4-(1-methyl-3-indolyl)-1H-pyrrole-2,5-dione, m.p. 276°–279° C.

EXAMPLE 8

0.058 g of 3-(5-hydroxy-1-methyl-3-indolyl)-4-(1-methyl-3-indolyl)furan-2,5-dione was treated with 1.5 ml of DMF and 20 ml of 33% aqueous ammonia and the mixture was heated at 140° C. for 3 hours. The solvent was removed from the cooled solution and the residue was triturated with water. The resulting solid was filtered off and dried to give 0.018 g of 3-(5-hydroxy-1-methyl-3-indolyl)-4-(1-methyl-3-indolyl)-1H-pyrrole-2,5-dione, m.p. 284°–287° C.

The furandione starting material was prepared as follows:

7.85 g of 5-methoxy-1-methylindole-3-glyoxylyl chloride in 100 ml of dichloromethane was treated with 10.8 ml of triethylamine followed by 5.86 g of 1-methylindol-3-ylacetic acid. After 16 hours the mixture was concentrated and the residue was chromatographed on silica gel with 1% methanol in dichloromethane.

0.10 g of the obtained 3-(5-methoxy-1-methyl-3-indolyl)-4-(1-methyl-3-indolyl)furan-2,5-dione (m.p. 234°–237° C.) was treated with 3 ml of pyridine and 0.40 g of pyridine hydrochloride and the mixture was heated at 220° C. for 3 hours. The mixture was partitioned between dichloromethane and water and the organic phase was washed with water and then with 0.5M hydrochloric acid. The organic phase was dried and concentrated. The residue was chromatographed on silica gel with 1% methanol in dichloromethane. There was obtained 0.058 g of furandione, m.p. 128°–132° C.

EXAMPLE 9

A solution of 800 mg of 3-(1-methyl-3-indolyl)-4-(1-methyl-2-pyrrolyl)furan-2,5-dione in 6 ml of DMF and 50 ml of 33% aqueous ammonia was heated to 130° C. for 3 hours. The precipitate was filtered off and dried to yield 400 mg of 3-(1-methyl-3-indolyl)-4-(1-methyl-2-pyrrolyl)-1H-pyrrole-2,5-dione, m.p. 248°–250° C.

The furandione starting material was prepared as follows:

To 6.4 g of 1-methylindole-3-glyoxylyl chloride in 120 ml of dichloromethane and 8.0 ml of triethylamine were added 4.0 g of 1-methylpyrrole-2-acetic acid under a nitrogen atmosphere. After stirring for 16 hours the solvent was evaporated. The residue was purified on silica gel with ethyl acetate/petroleum ether (1:2) to give 800 mg of the furandione, m.p. 163°–165° C.

EXAMPLE 10

1.4 ml of acetaldehyde dimethyl acetal and 10 mg of p-toluenesulphonic acid were added to a solution of 250 mg of 3,4-bis(3-indolyl)-1H-pyrrole-2,5-dione in 40 ml of chloroform. The resulting mixture was heated to reflux for 18 hours under nitrogen. The obtained solution was evaporated and the residue was purified on silica gel with ethyl acetate/petroleum ether (1:2). Recrystallization from chloroform/hexane gave 165 mg of 3,4-bis[1-(1-methoxyethyl)-3-indolyl]-1H-pyrrole-2,5-dione, m.p. 222°–224° C.

EXAMPLE 11

220 mg of thiophenol and 1 drop of concentrated hydrochloric acid were added to a solution of 150 mg of the product of Example 10 in 40 ml of dichloromethane. The solution was stirred nitrogen for 2 hours. The solvent was evaporated and the residue was recrystallized from diethyl ether/hexane to give 190 mg of 3,4-bis[1-(1-phenylthioethyl)-3-indolyl]-1H-pyrrole-2,5-dione, m.p. 102°–105° C.

EXAMPLE 12

A solution of 4.12 g of 2-methylindole in 75 ml of benzene was treated with 9.2 ml of a 3M solution of methylmagnesium iodide in diethyl ether and the resulting solution was stirred under nitrogen for 0.5 hour. 2.0 g of dibromomaleimide were added and the mixture was heated to reflux for 14 hours. The cooled mixture was evaporated, dissolved in 200 ml of dichloromethane and acidified with 100 ml of 2M hydrochloric acid. The organic layer was separated, washed with 100 ml of water, dried and evaporated. The residue was triturated with dichloromethane and the obtained solid was recrystallized from acetone/water to give 1.1 g of 3,4-bis(2-methyl-3-indolyl)-1H-pyrrole-2,5-dione, m.p. 311°–313° C.

EXAMPLE 13

20 ml of a 1M solution of $LiAlH_4$ in diethyl ether was added to a solution of 1.0 g of 3,4-bis(3-indolyl)-1H-pyrrole-2,5-dione in 140 ml of THF. The mixture was stirred for 18 hours under nitrogen. The mixture was cooled to 0° C., quenched with 50 ml of water, then acidified to pH 2 with 2M hydrochloric acid and extracted with ethyl acetate. The organic extracts were washed with saturated sodium bicarbonate solution, dried and evaporated. The residue was purified on silica gel with 5–10% methanol in dichloromethane. The first product eluted was triturated with ethyl acetate/hexane to give 175 mg of 3,4-bis(3-indolyl)-3-pyrrolin-2-one, m.p. 290°–293° C. (decomposition). The second product eluted was crystallized from ethyl acetate/chloroform to give 490 mg of 5-hydroxy-3,4-bis(3-indolyl)-3-pyrrolin-2-one, m.p. above 250° C. (decomposition).

The pyrroledione starting material was prepared as follows:

A solution of 18.72 g of indole in 240 ml of benzene was treated with 48 ml of a 3M solution of methylmagnesium iodide in diethyl ether and stirred under nitrogen for 0.5 hour. 10.2 g of dibromomaleimide were added and the mixture was heated to reflux for 65 hours, cooled and then evaporated. The residue was partitioned between dichloromethane and 2M hydrochloric acid and the insoluble material was filtered off. The dichloromethane extract was separated and dried and the solvent was evaporated. The product was purified on silica gel with ethyl acetate/petroleum ether to give 6.0 g of the pyrroledione, m.p. 252°–253° C. after precipitation from methanol/water.

EXAMPLE 14

820 mg of Lawesson's reagent was added to a solution of 330 mg of 3,4-bis(3-indolyl)-1H-pyrrole-2,5-dione in 50 ml of dimethoxyethane and the mixture was heated to reflux for 1 hour. 410 mg of Lawesson's reagent were then added and the mixture was heated to reflux for a further 1 hour. The solvent was evaporated and the residue was purified on silica gel with ethyl acetate/hexane (1:4). Recrystallization from diethyl ether/hexane gave 30 mg of 5-thioxo-3,4-bis(3-indolyl)-3-pyrrolin-2-one, m.p. 254°–257° C.

EXAMPLE 15

260 mg of a 60% dispersion of sodium hydride in mineral oil were added to a solution of 295 mg of benzimidazole in 10 ml of DMF and the mixture was stirred under nitrogen for 0.5 hour. 582 mg of 3-bromo-4-(3-indolyl)-1H-pyrrole-2,5-dione were added and the mixture was heated to 50° C. for 18 hours. A solution of 767 mg of benzimidazole and 260 mg of sodium hydride in 10 ml of DMF was added and the mixture was heated to 90° C. for 18 hours under nitrogen. The solvent was evaporated and the residue was partitioned between dichloromethane and 2M hydrochloric acid. The precipitate was purified on silica gel with ethyl acetate/petroleum ether. Recrystallization from ethyl acetate gave 25 mg of 3-(1-benzimidazolyl)-4-(3-indolyl)-1H-pyrrole-2,5-dione, m.p. 310°–320° C.

The starting pyrroledione was prepared as follows:

A solution of 2.34 g of indole in 25 ml of benzene was treated with 13.4 ml of a 3M solution of methylmagnesium bromide in diethyl ether. The solution was stirred under nitrogen for 0.5 hour and then was added to a solution of 5.12 g of dibromomaleimide in 75 ml of benzene. The mixture was stirred for 16 hours, evaporated and the residue was partitioned between dichloromethane and 2M hydrochloric acid. The precipitate was filtered off and triturated with diethyl ether to give 1.8 g of the desired material, m.p. 204°–205° C., after recrystallization from ethyl acetate/petroleum ether.

EXAMPLE 16

A solution of 804 mg of 3-(1-methyl-3-indolyl)-4-[1-methyl-2-(methylthio)-3-indolyl]furan-2,5-dione in 12 ml of DMF and 50 ml of 33% aqueous ammonia was heated to 130° C. for 2 hours. The product was filtered off and dried to give 675 mg of 3-(1-methyl-3-indolyl)-4-[1-methyl-2-(methylthio)-3-indolyl]-1H-pyrrole-2,5-dione, m.p. 281°–283° C.

The starting furandione was prepared as follows:

1.40 g of oxalyl chloride were added to a solution of 1.77 g of 1-methyl-2-methylthioindole in 45 ml of dichloromethane at 0° C. The solution was allowed to warm to room temperature and the solvent was evaporated. To a solution of the product in dichloromethane were added 2.02 g of triethylamine and 1.89 g of 1-methylindol-3-ylacetic acid under nitrogen. After stirring for 18 hours the solvent was evaporated. The residue was purified on silica gel with ethyl acetate/hexane to give 1.32 g of the furan-2,5-dione, m.p. 230°–232° C., after recrystallization from dichloromethane/hexane.

EXAMPLE 17

270 mg of m-chloroperbenzoic acid were added to a stirred solution of 500 mg of the product of Example 16 in 250 ml of dichloromethane at 0° C. The solution was stirred at 0° C. for 1 hour and then washed with a saturated sodium bicarbonate solution and water. The solution was dried. The residue was triturated with methanol to give 505 mg of 3-(1-methyl-3-indolyl)-4-[1-methyl-2-(methylsulphinyl)-3-indolyl]-1H-pyrrole-2,5-dione, m.p. 300° C.

EXAMPLE 18

A solution of 4.9 g of indole in 50 ml of benzene was treated with 19 ml of a 3M solution of methylmagnesium iodide in diethyl ether and stirred under nitrogen for 15 minutes. 3.5 g of 3-bromo-4-phenyl-1H-pyrrole-2,5-dione were added and the mixture was stirred for 18 hours. The solvent was evaporated and the residue was dissolved in 250 ml of dichloromethane and 50 ml of 2M hydrochloric acid. The organic extracts were washed with water, dried and evaporated. The residue was purified on silica gel with ethyl acetate/petroleum ether. Trituration with dichloromethane and recrystallization from methanol yielded 1.40 g of 3-(3-indolyl)-4-phenyl-1H-pyrrole-2,5-dione, m.p. 256° C.

The starting pyrroledione was prepared as follows:

5.0 g of phenyl succinimide were heated to 100° C. and 3.1 ml of bromine were added dropwise. The temperature was then increased to 120° C. for 15 minutes. After cooling 25 ml of water were added and the mixture was stirred for 10 minutes before the product was filtered off. Recrystallization from ethanol/water gave 3.55 g of the desired product, m.p. 181° C.

EXAMPLE 19

To a suspension of 105 mg of indole in 20 ml of benzene were added 0.6 ml of a 3M solution of methylmagnesium bromide in diethyl ether under nitrogen. The mixture was stirred for 0.5 hour. 100 mg of 3-bromo-4-(5-methoxy-3-indolyl)-1H-pyrrole-2,5-dione were added and the mixture was heated to reflux for 5 days. After cooling the residue was partitioned between dichloromethane and 2M hydrochloric acid. The organic extracts were washed with water, dried and evaporated. The residue was purified on silica gel with 1% methanol in dichloromethane and then with 50% methanol/0.1% trifluoroacetic acid/water on Spherisorb to give 3 mg of 3-(3-indolyl)-4-(5-methoxy-3-indolyl)-1H-pyrrole-2,5-dione, m.p. 280° C.

The 3-bromo-4-(5-methoxy-3-indolyl)-1H-pyrrole-2,5-pyrroldione starting material was prepared as follows:

4.0 ml of a 3M solution of methylmagnesium bromide in diethyl ether was added to a solution of 2.00 g of 5-methoxyindole in 25 ml of benzene under nitrogen. The resulting solution was stirred for 0.5 hour. After addition of 0.87 g of dibromomaleimide the mixture was heated to reflux for 24 hours. After cooling the solvent was evaporated and the residue was partitioned between dichloromethane and 2M hydrochloric acid. The organic extracts were washed with water, dried and evaporated. The residue was purified on silica gel with 5% methanol in dichloromethane, 2% methanol in dichloromethane and ethylacetate/petroleum ether (1:2) to give 100 mg of the pyrroledione, m.p. 225° C. (decomposition).

EXAMPLE 20

1.4 ml of a 3M solution of methylmagnesium iodide in diethyl ether was added to a solution of 360 mg indole in 20 ml of benzene under nitrogen. After stirring at room temperature for 10 minutes 300 mg of 3-bromo-4-(4-nitrophenyl)-1H-pyrrole-2,5-dione were added and the resulting mixture was heated to reflux for 4 days. After cooling the solution was evaporated and the residue was partitioned between dichloromethane and 2M hydrochloric acid. The organic phase was washed with water, dried and evaporated. The residue was purified on silica gel with dichloromethane and 1% methanol in dichloromethane and then with 20% methanol/water on Hypersil to give 3 mg of 3-(3-indolyl)-4-(4-nitrophenyl)-1H-pyrrole-2,5-dione, m.p. 125° C. (decomposition).

The pyrroledione starting material was prepared as follows:

To a solution of 2.33 g of p-nitrophenyl succinimide in 150 ml of diethyl ether were added 1.2 ml of bromine. The solution was heated to reflux for 4 days, with a further 1.2 ml of bromine being added after the first day and again after the second day. After cooling the mixture was washed with saturated sodium thiosulphate and with water, dried and evaporated. The residue was purified on silica gel with diethyl ether/petroleum ether. Recrystallization from toluene gave 350 mg of the pyrroledione, m.p. 165° C.

EXAMPLE 21

A solution of 200 mg of 3-[1-(3-acetoxypropyl)-3-indolyl]-4-(1-methyl-3-indolyl)furan-2,5-dione in 1 ml of DMF and 2 ml of 33% aqueous ammonia was heated to 100° C. for 2 hours. 50 ml of water were added and the resulting solid was filtered off, dried and recrystallized from ethyl acetate to give 85 mg of 3-[1-(3-hydroxypropyl)-3-indolyl]-4-(1-methyl-3-indolyl)-1H-pyrrole-2,5-dione, m.p. 185°–187° C.

The furandione starting material was prepared as follows:

367 μl of oxalyl chloride were added to a solution of 868 mg of 1-(3-acetoxypropyl)indole in 10 ml of dichloromethane at 0° C. The solution was stirred for 3 hours and the solvent was then evaporated. The residue was dissolved in dichloromethane and triethylamine and 756 mg of 1-methylindol-3-ylacetic acid were added under nitrogen. After stirring for 18 hours the solvent was evaporated and the residue was purified on silica gel with ethyl acetate/petroleum ether. Recrystallization from ethyl acetate/hexane gave 290 mg of the furandione, m.p. 94°–96° C.

EXAMPLE 22

A solution of 200 mg of 3-[1-(2-methoxycarbonylethyl)-3-indolyl]-4-(1-methyl-3-indolyl)furan-2,5-dione in 1 ml of DMF and 2 ml of 33% aqueous ammonia was heated to 100° C. for 0.75 hour. 30 ml of ethyl acetate were added to the cooled solution and the organic phase was separated and washed with saturated sodium bicarbonate solution. The organic phase was dried and the solvent was evaporated. Recrystallization from ethyl acetate/petroleum ether gave 40 mg of 3-[1-(2-carbamoylethyl)-3-indolyl]-4-(1-methyl-3-indolyl)-1H-pyrrole-2,5-dione, m.p. 243°–247° C.

The furandione starting material was prepared as follows:

A solution of 622 μl of oxalyl chloride and 1.5 g of 1-[2-(methoxycarbonyl)ethyl]indole in 20 ml of dichloromethane was stirred at 0° C. for 10 minutes and then at room temperature for 2 hours, whereupon the solvent was evaporated. The residue was dissolved in dichloromethane and 2.03 ml of triethylamine and 1.4 g of 1-methylindol-3-ylacetic acid were added under nitrogen. After stirring for 18 hours the solvent was evaporated and the residue was purified on silica gel with dichloromethane and then ethyl acetate/petroleum ether. Recrystallization from ethyl acetate/petroleum ether gave 590 mg of the furandione, m.p. 150°–152° C.

EXAMPLE 23

A solution of 150 mg of 3-[1-(2-carboxyethyl)-3-indolyl]-4-(1-methyl-3-indolyl)furan-2,5-dione in 1 ml of DMF and 2 ml of 33% aqueous ammonia was heated to 100° C. for 1 hour. The cooled solution was evaporated and the residue was crystallized from ethyl acetate/petroleum ether to give 90 mg of 3-[1-(2-carboxyethyl)-3-indolyl]-4-(1-methyl-3-indolyl)-1H-pyrrole-2,5-dione, m.p. 256°–258° C.

The furandione starting material was prepared as follows:

A solution of 200 mg of 3-[1-(2-methoxycarbonylethyl)-3-indolyl]-4-(1-methyl-3-indolyl)furan-2,5-dione in 4 ml of ethanol was heated to reflux for 1 hour with 180 mg of KOH. The solvent was evaporated and the residue was acidified with 2M hydrochloric acid and extracted with dichloromethane. The organic phase was separated, dried and evaporated. The residue was triturated with ethyl acetate to give 170 mg of the furandione, m.p. 222°–224° C.

EXAMPLE 24

A solution of 40 mg of the product of Example 23 in 5 ml of methanol was heated to reflux for 4 hours with 10 mg of p-toluenesulphonic acid. The solvent was evaporated and the residue was crystallized from ethyl acetate to give 25 mg of 3-[1-(2-methoxycarbonylethyl)-3-indolyl]-4-(1-methyl-3-indolyl)-1H-pyrrole-2,5-dione, m.p. 209°–211° C.

EXAMPLE 25

A solution of 2.50 g of 3-[1-(3-azidopropyl)-3-indolyl]-4-(1-methyl-3-indolyl)furan-2,5-dione in 13 ml of DMF and 18 ml of 33% aqueous ammonia was heated to 140° C. for 4 hours. The product was filtered off from the cooled mixture to give 2.27 g of 3-[1-(3-azidopropyl)-3-indolyl]-4-(1-methyl-3-indolyl)-1H-pyrrole-2,5-dione, m.p. 222°–224° C.

The furandione starting material was prepared as follows:

a) To a solution of 23.4 g of indole in 200 ml of DMF, cooled to 10° C., were added 22.4 g of potassium hydroxide and 101 g of 1,3-dibromopropane. The mixture was stirred under nitrogen for 3 days. The solid formed was filtered off and the filtrate was evaporated. The residue was chromatographed on silica gel with 5% diethyl ether in petroleum ether to give 14.7 g of 1-(3-bromopropyl)indole.

b) 4.2 ml of oxalyl chloride were added to a solution of 11.75 g of 1-(3-bromopropyl)indole in 125 ml of dichloromethane at 0° C. The solution was stirred at room temperature for 2 hours and the solvent was then evaporated. The residue was dissolved in dichloromethane and treated with 17.4 ml of diisopropylethylamine and 9.45 g of 1-methylindol-3-ylacetic acid under nitrogen. After stirring for 3 days the solvent was evaporated and the residue was purified on silica gel with dichloromethane. Recrystallization from ethyl acetate/petroleum ether gave 5.09 g of 3-[1-(3-bromopropyl)-3-indolyl]-4-(1-methyl-3-indolyl) furan-2,5-dione, m.p. 168°–170° C.

c) A solution of 2.8 g of the product of b) in 50 ml of DMF was stirred at room temperature for 2 hours and then at 60° C. for 2 hours with 1.25 g of sodium azide. The solvent was evaporated and the residue was partitioned between dichloromethane and water. The organic phase was washed with water, dried and evaporated. Crystallization from ethyl acetate gave 2.5 g of the desired furandione, m.p. 154°–156° C.

EXAMPLE 26 a) A solution of 1.9 g of the product of Example 25 in 300 ml of ethyl acetate was hydrogenated over 190 mg of 10% Pd/C for 3 days. The solution was filtered and the filtrate was concentrated by evaporation. The resulting precipitate was filtered off and dried to give 1.57 g of 3-[1-(3-aminopropyl)-3-indolyl]-4-(1-methyl-3-indolyl)-1H-pyrrole-2,5-dione, m.p. 195°–197° C.

b) 1.3 g of the product of a) were taken up in 500 ml of ethyl acetate and treated with a saturated solution of hydrogen chloride in ethyl acetate until no further precipitate was observed. The mixture was stirred for 2 hours and then filtered to give 1.5 g of 3-[1-(3-aminopropyl)-3-indolyl]-4-(1-methyl-3-indolyl)-1H-pyrrole-2,5-dione hydrochloride, m.p. 215°–220° C.

EXAMPLE 27

40 mg of a 60% suspension of sodium hydride in mineral oil was added to a solution of 327 mg of 3,4-bis-(3-indolyl)-1H-pyrrole-2,5-dione in 5 ml of DMF at 0° C. under nitrogen. After 0.5 hour the mixture was cooled to −20° C. and 108 mg of trimethylsilyl chloride were added. The mixture was allowed to warm to room temperature, then cooled to 0° C. and then a further 80 mg of sodium hydride were added thereto. After 0.5 hour at 0° C. 116 mg of propylene oxide were added and the mixture was stirred overnight. 5 ml of water were added and the mixture was extracted with dichloromethane. The organic phase was dried and evaporated. The residue was purified on silica gel with ethyl acetate/petroleum ether. Recrystallization from diethyl ether/petroleum ether gave 30 mg of 3,4-bis[1-(2-hydroxypropyl)-3-indolyl]-1H-pyrrole-2,5-dione, m.p. 133°–135° C.

EXAMPLE 28

3,4-Bis(1-methoxymethyl-3-indolyl)-1H-pyrrole-2,5-dione, m.p. 178°–182° C. was manufactured in an analogous manner to that described in Example 10.

EXAMPLE 29

In an analogous manner to that described in Example 11 there were manufactured:

3,4-Bis[1-[1-(1-hydroxyethylthio)ethyl]-3-indolyl]-1H-pyrrole-2,5-dione, m.p. 191°–194° C.;

3,4-bis[1-[1-(2-mercaptoethylthio)ethyl]-3-indolyl]-1H-pyrrole-2,5-dione, m.p. 97°–99° C.; and 3,4-bis[1-[1-(carboxymethylthio)ethyl]-3-indolyl]-1H-pyrrole-2,5-dione, m.p. 111°–114° C.

EXAMPLE 30

In an analogous manner to that described in Example 16 there were manufactured:

3,4-Bis(1-methyl-3-indolyl)-1H-pyrrole-2,5-dione, m.p. 355° C.;

3-(4-methoxy-1-methyl-3-indolyl)-4-(1-methyl-3-indolyl)-1H-pyrrole-2,5-dione, m.p. 288°–290° C.;

3-(1-methyl-5-methylthio-3-indolyl)-4-(1-methyl-3-indolyl)-1H-pyrrole-2,5-dione, m.p. 260° C.;

3-(6-methoxy-1-methyl-3-indolyl)-4-(1-methyl-3-indolyl)-1H-pyrrole-2,5-dione, m.p. 267° C.;
3-(7-methoxy-1-methyl-3-indolyl)-4-(1-methyl-3-indolyl)-1H-pyrrole-2,5-dione, m.p. 255° C.;
3,4-bis(1-benzyl-3-indolyl)-1H-pyrrole-2,5-dione, m.p 108° C.; and
3-(5-chloro-1-methyl-3-indolyl)-4-(1-methyl-3-indolyl)-1H-pyrrole-2,5-dione of m.p. 270°–271° C.

EXAMPLE 31

3-(1-Methyl-5-methylsulphinyl-3-indolyl)-4-(1-methyl-3-indolyl)-1H-pyrrole-2,5-dione, m.p. 292° C. was manufactured in an analogous manner to that described in Example 17.

EXAMPLE 32

In an analogous manner to that described in Example 21 there were manufactured:
3-[1-(4-Hydroxybutyl)-3-indolyl]-4-(1-methyl-3-indolyl)-1H-pyrrole-2,5-dione, m.p. 185°–188° C.;
3-(1-alpha-D-glucopyranosyl-3-indolyl)-4-(1-methyl-3-indolyl)-1H-pyrrole-2,5-dione, m.p. 210°–215° C.;
3,4-bis[1-(4-hydroxybutyl-3-indolyl)]-1H-pyrrole-2,5-dione, m.p. 192°–193° C.; and
3-[1-(5-hydroxypentyl)-3-indolyl]-4-(1-methyl-3-indolyl)-1H-pyrrole-2,5-dione, m p. 179°–181° C.

EXAMPLE 33

3-[1-(4-Carbamoylbutyl)-3-indolyl]-4-(1-methyl-3-indolyl)-1H-pyrrole-2,5-dione, m.p. 247°–249° C. was manufactured in an analogous manner to that described in Example 22.

EXAMPLE 34

In an analogous manner to that described in Example 23 there were manufactured:
3-[1-(3-Carboxypropyl)-3-indolyl]-4-(1-methyl-3-indolyl)-1H-pyrrole-2,5-dione, m.p. 238°–240° C.; and
3-[1-(4-carboxybutyl)-3-indolyl]-4-(1-methyl-3-indolyl)-1H-pyrrole-2,5-dione, m.p. 234°–238° C.

EXAMPLE 35

In an analogous manner to that described in Example 24 there were manufactured:
3-[1-[3-(Methoxycarbonyl)propyl]-3-indolyl]-4-(1-methyl-3-indolyl)-1H-pyrrole-2,5-dione, m.p. 208°–210° C.; and
3-[1-[4-(methoxycarbonyl)butyl]-3-indolyl]-4-(1-methyl-3-indolyl)-1H-pyrrole-2,5-dione, m.p. 138°–140° C.

EXAMPLE 36

In an analogous manner to that described in Example 25 there were manufactured:
3-[1-(4-Azidobutyl)-3-indolyl]-4-(1-methyl-3-indolyl)-1H-pyrrole-2,5-dione, m.p. 196°–198° C.; and
3-[1-(5-azidopentyl)-3-indolyl]-4-(1-methyl-3-indolyl)-1H-pyrrole-2,5-dione, m.p. 170°–172° C.

EXAMPLE 37

In an analogous manner to that described in Example 1 there were manufactured:
3-(1-Benzyl-3-indolyl)-4-(1-methyl-3-indolyl)-1H-pyrrole-2,5-dione, m.p. 261°–262° C.;
3-(5-methoxy-1-methyl-3-indolyl)-4-(1-methyl-3-indolyl)-1H-pyrrole-2,5-dione, m.p. 240°–245° C.;
3-(5-benzyloxy-1-methyl-3-indolyl)-4-(1-methyl-3-indolyl)-1H-pyrrole-2,5-dione, m.p. 215°–218° C.;
3-(1-methyl-3-indolyl)-4-(1-methyl-7-nitro-3-indolyl)-1H-pyrrole-2,5-dione, m.p. 264°–266° C.;
3-(1-methyl-3-indolyl)-4-(1-methyl-6-nitro-3-indolyl)-1H-pyrrole-2,5-dione, m.p. 285°–287° C.;
3-(1-methyl-3-indolyl)-4-(1,5-dimethyl-3-indolyl)-1H-pyrrole-2,5-dione, m.p. 283°–285° C.;
3-(1,7-dimethyl-3-indolyl)-4-(1-methyl-3-indolyl)-1H-pyrrole-2,5-dione, m.p. >300° C.;
3-(6-chloro-1-methyl-3-indolyl)-4-(1-methyl-3-indolyl)-1H-pyrrole-2,5-dione, m.p. 280°–282° C.;
3-(1-methyl-3-indolyl)-4-(1-methyl-4-nitro-3-indolyl)-1H-pyrrole-2,5-dione, m.p. 315°–316° C.; and
3-(1,4-dimethyl-3-indolyl)-4-(1-methyl-3-indolyl)-1H-pyrrole-2,5-dione, m.p 292°–293° C.

EXAMPLE 38

In an analogous manner to that described in Example 3 there were manufactured:
3-(1-Methyl-3-indolyl)-4-phenyl-1H-pyrrole-2,5-dione, m.p. 243° C. (decomposition);
3-(4-methoxyphenyl)-4-(1-methyl-3-indolyl)-1H-pyrrole-2,5-dione, m.p 262° C.;
3-(4-chlorophenyl)-4-(1-methyl-3-indolyl)-1H-pyrrole-2,5-dione, m.p. 268°–270° C.;
3-(1-methyl-3-indolyl)-4-[4-(methylthio)phenyl]-1H-pyrrole-2,5-dione, m.p. 266°–267° C.;
3-(1-methyl-3-indolyl)-4-(2-nitrophenyl)-1H-pyrrole-2,5-dione, m.p. 230°–231° C.;
3-(4-aminophenyl)-4-(1-methyl-3-indolyl)-1H-pyrrole-2,5-dione, m.p. 297° C.;
3-(1-methyl-3-indolyl)-4-(3-nitrophenyl)-1H-pyrrole-2,5-dione, m.p. 248° C.;
3-(3-chlorophenyl)-4-(1-methyl-3-indolyl)-1H-pyrrole-2,5-dione, m.p. 224°–225° C.;
3-(1-methyl-3-indolyl)-4-(2-methylphenyl)-1H-pyrrole-2,5-dione, m.p. 245°–247° C.;
3-(3-bromophenyl)-4-(1-methyl-3-indolyl)-1H-pyrrole-2,5-dione, m.p. 219°–220° C.;
3-(2,5-dimethylphenyl)-4-(1-methyl-3-indolyl)-1H-pyrrole-2,5-dione, m.p. 262°–263° C.;
3-(2-chlorophenyl)-4-(1-methyl-3-indolyl)-1H-pyrrole-2,5-dione, m.p. 238°–239° C.;
3-(1-methyl-3-indolyl)-4-(2-trifluoromethylphenyl)-1H-pyrrole-2,5-dione, m.p. 237°–238° C.; and
3-(1-methyl-3-indolyl)-4-(3-trifluoromethylphenyl)-1H-pyrrole-2,5-dione, m.p. 187°–188° C.

EXAMPLE 39

3-(1-Methyl-3-indolyl)-4-(2-naphthyl)-1H-pyrrole-2,5-dione, m.p. 289° C. (decomposition) was manufactured in an analogous manner to that described in Example 2.

EXAMPLE 40

3-(1-Methyl-3-indolyl)-4-(2-thienyl)-1H-pyrrole-2,5-dione, m.p. 244°–246° C. was manufactured in an analogous manner to that described in Example 5.

EXAMPLE 41

In an analogous manner to that described in Example 6 there were manufactured:
3-(7-Amino-1-methyl-3-indolyl)-4-(1-methyl-3-indolyl)-1H-pyrrole-2,5-dione, m.p. >300° C.;
3-(6-amino-1-methyl-3-indolyl)-4-(1-methyl-3-indolyl)-1H-pyrrole-2,5-dione, m.p. 264°–267° C.; and 3-(3-aminophenyl)-4-(1-methyl-3-indolyl)-1H-pyrrole-2,5-dione, m.p. 259° C.

EXAMPLE 42

In an analogous manner to that described in Example 7 there were manufactured:

3-(7-Acetamido-1-methyl-3-indolyl)-4-(1-methyl-3-indolyl)-1H-pyrrole-2,5-dione, m.p. >300° C.; and 3-(6-acetamido-1-methyl-3-indolyl)-4-(1-methyl-3-indolyl)-1H-pyrrole-2,5-dione, m.p. >300° C.

EXAMPLE 43

In an analogous manner to that described in Example 17 there were manufactured:

3-(1-Methyl-3-indolyl)-4-[4-(methylsulphonyl)phenyl]-1H-pyrrole-2,5-dione, m.p. 265° C.; and 3-(1-methyl-3-indolyl)-4-[4-(methylsulphinyl)phenyl]-1H-pyrrole-2,5-dione, m.p. 256°–258° C.

EXAMPLE 44

In an analogous manner to that described in Example 1 there were manufactured:

3-(1-Methyl-3-indolyl)-4-(1,2-dimethyl-3-indolyl)-1H-pyrrole-2,5-dione, m.p. 305°–306° C.; and 3-(1-methyl-2-indolyl)-4-(1-methyl-3-indolyl)-1H-pyrrole-2,5-dione, m.p. >300° C.

EXAMPLE 45

In an analogous manner to that described in Example 3 there were manufactured:

3-(1-Methyl-3-indolyl)-4-(2,3-dimethylphenyl)-1H-pyrrole-2,5-dione, m.p. 275°–276° C.;

3-(3,5-dichlorophenyl)-4-(1-methyl-3-indolyl)-1H-pyrrole-2,5-dione, m.p. 197°–200° C.;

3-(2,3,6-trichlorophenyl)-4-(1-methyl-3-indolyl)-1H-pyrrole-2,5-dione, m.p. 306°–309° C.; and 3-(2,6-dichlorophenyl)-4-(1-methyl-3-indolyl)-1H-pyrrole-2,5-dione, m.p. 285°–286° C.

EXAMPLE 46

A mixture, 163 mg of 3-(1-indolyl)-4-(1-methyl-3-indolyl)furan-2,5-dione, 2.6 g of hexamethyldisilazane, 0.6 g of methanol and 50 ml of toluene was stirred at 40° C. for 1 hour and then at 110° C. for 1 hour. The mixture was evaporated and the residue was chromatographed on silica gel with 10% methanol in dichloromethane to give 75 mg of 3-(1-indolyl)-4-(1-methyl-3-indolyl)-1H-pyrrole-2,5-dione, m.p. 235°–236° C.

The furandione starting material was prepared as follows: 876 mg of indol-1-ylacetic acid in 50 ml of dichloromethane were treated firstly with 1.65 ml of diisopropylethylamine and then with a solution of 1.10 g of 1-methylindole-3-glyoxylyl chloride in 50 ml of dichoromethane. The mixture was stirred for 3 hours and then concentrated. The residue was chromatographed on silica gel with dichloromethane to give 430 mg of the furandione, m.p. 164°–166° C.

EXAMPLE 47

3-(3-Benzofuranyl)-4-(1-methyl-3-indolyl)-1H-pyrrole-2,5-dione, m.p. 183°–185° C. was manufactured in an analogous manner to that described in Example 46.

EXAMPLE 48

200 mg of the product of Example 26b) in 10 ml of DMF were treated with a solution of 85 mg of 1,1'-thiocarbonyldiimidazole in 2 ml of THF and the mixture was stirred for 16 hours. The solvents were then evaporated and the residue was chromatographed on silica gel with 10% methanol in dichloromethane to give 129 mg of 3-[1-(3-isothiocyanatopropyl)-3-indolyl]-4-(1-methyl-3-indolyl)-1H-pyrrole-2,5-dione, m.p. 219°–221° C.

EXAMPLE 49

A solution of 100 mg of the product of Example 26b) in 10 ml of DMF was treated with a solution of 40 mg of 1,1'-carbonyldiimidazole in 2 ml of THF. The mixture was stirred for 16 hours. The solvents were evaporated and the residue was chromatographed on silica gel with chloroform/methanol/acetic acid/water (60:18:2:3) to give 90 mg of 3-[1-[3-(1-imidazolylcarboxamido)propyl]-3-indolyl]-4-(1-methyl-3-indolyl)-1H-pyrrole-2,5-dione, m.p. 145°–148° C.

EXAMPLE 50

A suspension of 500 mg of the product of Example 26b) in 100 ml of ethanol was added to a mixture of 116 mg of sodium carbonate and 177 mg of dimethyl N-cyanodithioiminocarbonate. After 16 hours a further 160 mg of dimethyl N-cyanodithioiminocarbonate were added and stirring was continued for 2 days. The solvent was evaporated and the residue was chromatographed on silica gel with firstly dichloromethane and then ethyl acetate to give 120 mg of 3-[1-[(3-cyano-2-methylisothioureido)propyl]-3-indolyl]-4-(1-methyl-3-indolyl)-1H-pyrrole-2,5-dione, m.p. 236°–238° C.

EXAMPLE 51

A solution of 200 mg of the product of Example 26a) in 10 ml of DMF was treated with a solution of 83 mg of 1,1-bis(methylthio)-2-nitroethylene in 10 ml of acetonitrile and the mixture was heated at 85° C. for 3 days. Evaporation of the solvent and chromatography of the residue on silica gel with 10% methanol in dichloromethane gave 154 mg of 3-(1-methyl-3-indolyl)-4-[1-[3-[[1-(methylthio)-2-nitrovinyl]amino]propyl]-3-indolyl]-1H-pyrrole-2,5-dione, m.p. 144°–146° C.

EXAMPLE 52

A solution of 175 mg of the product of Example 49 in 10 ml of DMF was treated with 10 ml of ethanolic ammonia. The mixture was stirred for 3 hours and then the solvents were evaporated. The residue was crystallized from ethanol to give a solid which was purified on silica gel with 1% to 20% methanol in dichloromethane to give 43 mg of 3-(1-methyl-3-indolyl)-4-[1-(3-ureidopropyl)-3-indolyl]-1H-pyrrole-2,5-dione, m.p. 248°–250° C.

EXAMPLE 53

A solution of 150 mg of 3,5-dimethylpyrazole-1-carboxamidine nitrate in 10 ml of ethanol was treated with 200 mg of the product of Example 26a) and the mixture was heated at reflux for 3 days. The solvent was evaporated and the residue was chromatographed on silica gel with dichloromethane/methanol/acetic acid/water (60:18:2:3) to give 53 mg of 3-[1-(3-guanidinopropyl)-3-indolyl]-4-(1-methyl-3-indolyl)-1H-pyrrole-2,5-dione nitrate, m.p. 179°–181° C.

EXAMPLE 54

A solution of 0.411 g of 3-[1-(3-acetoxypropyl)-3-indolyl]-4-(2-nitrophenyl)furan-2,5-dione in 50 ml of chloroform was treated with a mixture of 1.53 g of 1,1,1,3,3,3-hexamethyldisilazane and 0.3 g of methanol and the mixture was heated at 60° C. for 1 hour. A further 1.53 g of hexamethyldisilazane and a further 0.3 g of methanol were added and the heating was continued overnight before adding further 1.53 g of hexamethyldisilazane and 0.3 g of methanol. The mixture was heated for a further 1 hour. The solvents were removed under reduced pressure and the residue was chromatographed on silica gel with 5% methanol in dichloromethane to give 130 mg of 3-[1-(3-acetoxypropyl)-3-indolyl]-4-(2-nitrophenyl)-1H-pyrrole-2,5-dione, m.p. 77°–78° C.

The furandione starting material was prepared as follows:

3.2 g of oxalyl chloride were added to a solution of 5.0 g of 1-(3-acetoxypropyl)indole in 100 ml of dichloromethane at 0° C. The mixture was allowed to warm to room temperature and was stirred for 3 hours before it was evaporated. The obtained solid was treated with dichloromethane and 5.5 g of triethylamine followed by 3.9 g of 2-nitrophenylacetic acid. The mixture was stirred for 16 hours and the solvents were evaporated. The residue was chromatographed on silica gel with ethyl acetate to give the desired furandione.

EXAMPLE 55

A solution of 40 mg of sodium hydroxide in 5 ml of ethanol was added to a solution of 400 mg of the product of Example 54 in 10 ml of ethanol. After stirring for 3 hours the solvent was removed under reduced pressure and the residue was chromatographed on silica gel with 10% methanol in dichloromethane to give 190 mg of 3-[1-(3-hydroxypropyl)-3-indolyl]-4-(2-nitrophenyl)-1H-pyrrole-2,5-dione, m.p. 193°–195° C.

EXAMPLE 56

A solution of 128 mg of the product of Example 51 in 30 ml of ethanol was treated with 10 ml of a saturated solution of ammonia in ethanol and the mixture was heated at 80° C. for 3 hours. The solvent was removed under reduced pressure and the residue was chromatographed on silica gel with 10% methanol in dichloromethane to give 39 mg of 3-[1-[3-(1-amino-2-nitrovinylamino)propyl]-3-indolyl]-4-(1-methyl-3-indolyl)-1H-pyrrole-2,5-dione, m.p. 206°–209° C. (decomposition).

EXAMPLE 57

A suspension of 100 mg of the product of Example 48 in 10 ml of ethanol was treated with 4 ml of DMF and then with 10 ml of a saturated solution of ammonia in ethanol. The mixture was left to stand at room temperature for 1 hour and the solvent was then evaporated. The residue was crystallized from ethanol to give 18 mg of 3-(1-methyl-3-indolyl)-4-[1-(3-thioureidopropyl)-3-indolyl]-1H-pyrrole-2,5-dione, m.p. 166°–168° C. (decomposition).

EXAMPLE 58

190 mg of methanesulphonic anhydride were added to a solution of 399 mg of the product of Example 21 and 1 ml of pyridine in 40 ml of dichloromethane. After 2 hours a further 40 mg of methanesulphonic anhydride and 1 ml of pyridine were added and stirring was continued for 16 hours. The mixture was washed with water, dried and evaporated. Crystallization from ethyl acetate/hexane gave 350 mg of 3-(1-methyl-3-indolyl)-4-[1-[3-(methylsulphonyloxy)propyl]-3-indolyl]-1H-pyrrole-2,5-dione, m.p. 202°–204° C.

EXAMPLE 59

7 mg of a 80% dispersion of sodium hydride in mineral oil was added to a cooled solution of 23 mg of 2-mercaptoimidazole in 10 ml of DMF. The mixture was stirred for 0.5 hour while cooling. 100 mg of the product of Example 58 were added and the mixture was stirred for 2 hours while cooling. The mixture was then allowed to warm to room temperature and was stirred overnight. The solvents were removed under reduced pressure and the residue was chromatographed on silica gel with 10% methanol in dichloromethane to give 20 mg of 3-[1-[3-(2-imidazolylthio)propyl]-3-indolyl]-4-(1-methyl-3-indolyl)-1H-pyrrole-2,5-dione, m.p. 130°–132° C.

EXAMPLE 60

In an analogous manner to that described in Example 59, from 27 mg of 2-mercaptothiazoline and 100 mg of the product of Example 58, there were obtained 18 mg of 3-(1-methyl-3-indolyl)-4-[1-[3-(2-thiazolin-2-ylthio)propyl]-3-indolyl]-1H-pyrrole-2,5-dione m.p. 170°–173° C.

EXAMPLE 61

In an analogous manner to that described in Example 59, from 25 mg of 2-mercaptopyrimidine and 100 mg of the product of Example 58, there were obtained 45 mg of 3-(1-methyl-3-indolyl)-4-[1-[3-(2-pyrimidinylthio)propyl]-3-indolyl]-1H-pyrrole-2,5-dione, m.p. 125°–127° C.

EXAMPLE 62

To a solution of sodium methoxide, prepared from 51 mg of sodium and 20 ml of methanol, were added 315 mg of 2-mercaptopyridine N-oxide and 200 mg of the product of Example 58. The mixture was heated at 55° C. for 16 hours. The solvent was removed under reduced pressure and the residue was triturated with ethyl acetate. The obtained solid was washed with 2N sodium hydroxide and then with water. Chromatography on silica gel with 1% methanol in dichloromethane gave 49 mg of 2-[3-[3-[3-(1-methyl-3-indolyl-2,5-dioxo-1H-pyrrole-4-yl]-1-indolyl]propyl thio]pyridine 1-oxide, m.p. 165°–167° C.

EXAMPLE 63

100 mg of the product of Example 50 were heated with 30 ml of ethanol, 2 ml of DMF and 40 ml of a saturated solution of ammonia in ethanol at 100° C. for 16 hours. The solvents were removed under reduced pressure and the residue was chromatographed on silica gel with 1% methanol in dichloromethane to give 10 mg of 3-[1-[3-(2-cyanoguanidino)propyl]-3-indolyl]-4-(1-methyl-3-indolyl)-1H-pyrrole-2,5-dione, m.p. 168°–170° C.

EXAMPLE 64

A solution of 100 mg of 3-[1-(3-aminopropyl)-3-indolyl]-4-(1-methyl-3-indolyl)-1H-pyrrole-2,5-dione acetate, containing an extra equivalent of acetic acid, in 10 ml of dimethyl sulphoxide (DMSO) was treated with 35 mg of sodium bicarbonate and 36 mg of 2-chloro-3-nitropyridine. The mixture was heated at 60° C. for 1 hour and at 100° C. for 2 hours. The solution was allowed to cool, water was added and the precipitate was filtered off and chromatographed on silica gel with 1% to 5% methanol in dichloromethane. The product was purified further by crystallization from hexane/ethyl acetate to give 60 mg of 3-(1-methyl-3-indolyl)-4-[1-[3-(3-nitro-2-pyridylamino)propyl]-3-indolyl]-1H-pyrrole-2,5-dione, m.p. 218°–220° C.

EXAMPLE 65

In an analogous manner to that described in Example 64, from 100 mg of the product of Example 26a) and 36 mg of 2-chloro-5-nitropyridine there were obtained 45 mg of 3-(1-methyl-3-indolyl)-4-[1-[3-(5-nitro-2-pyridylamino)propyl]-3-indolyl]-1H-pyrrole-2,5-dione, m.p. 245°–247° C.

EXAMPLE 66

A mixture of 100 mg of 3-[1-(3-aminopropyl)-3-indolyl]-4-(1-methyl-3-indolyl)-1H-pyrrole-2,5-dione acetate, containing an extra equivalent of acetic acid, 75 mg of 2-chloropyrimidine and 100 mg of sodium carbonate in 100 ml of DMSO was heated at 80° C. for 2 hours. 50 ml of water were added to the cooled solution and the precipitate was filtered off and chromatographed on silica gel with 5% methanol in dichloromethane to give 60 mg of 3-(1-methyl-3-indolyl)-4-[1-[3-(2-pyrimidinylamino)propyl]-3-indolyl]-1H-pyrrole-2,5-dione, m.p. 214°–215° C.

EXAMPLE 67

A solution of 560 mg of the product of Example 26a), containing two equivalents of acetic acid, in 20 ml of DMF was treated with 180 mg of sodium bicarbonate and 300 mg of methyl 4-benzyloxybenzimidate hydrochloride at room temperature for 24 hours. The solvent was evaporated and the residue was chromatographed on silica gel with 1% to 10% methanol in dichloromethane to give 275 mg of 3-[1-[3-(4-benzyloxy-α-iminobenzylamino)propyl]-3-indolyl]-4-(1-methyl-3-indolyl)-1H-pyrrole-2,5-dione hydrochloride, m.p. 254°–256° C.

The methyl 4-benzyloxybenzimidate hydrochloride used above was prepared as follows:

A solution of 560 mg of 4-benzyloxybenzonitrile in 16 ml of THF and 0.2 ml of methanol, cooled to 0° C., was saturated with hydrogen chloride and kept at 4° C. for 16 hours. The precipitate was filtered off, washed with diethyl ether and dried to give 357 mg of methyl 4-benzyloxybenzimidate hydrochloride, m.p. 179°–180° C.

EXAMPLE 68

93 mg of methanesulphonic anhydride were added to a solution of 0.46 mmol of the product of Example 55 in 25 ml of dichloromethane. 0.5 ml of pyridine was added and the mixture was stirred for 0.5 hour, then washed with water, dried and concentrated. Chromatography of the residue on silica gel with 10% methanol in dichloromethane gave 160 mg of 3-[1-[3-(methylsulphonyloxy)propyl]-3-indolyl]-4-(2-nitrophenyl)-1H-pyrrole-2,5-dione, m.p. 177°–178° C.

EXAMPLE 69

50 mg of thiourea were added to a solution, heated at reflux, of 150 mg of the product of Example 68 in 15 ml of ethanol. The mixture was heated for 1 hour and the solvent was then evaporated. The residue was chromatographed on silica gel with 20% methanol in dichloromethane to give 10 mg of 3-[1-[3-(amidinothio)propyl]-3-indolyl]-4-(2-nitrophenyl)-1H-pyrrole-2,5-dione methanesulphonate, m.p. 164°–165° C.

EXAMPLE 70

150 mg of 3-(1-methyl-3-indolyl)-4-(1-phenyl-3-indolyl) furan-2,5-dione were treated with 3 ml of DMF and 10 ml of 33% aqueous ammonia at 80° C. for 4 hours. The mixture was cooled and extracted with ethyl acetate. The ethyl acetate extract was dried and concentrated. The residue was crystallized from ethyl acetate/hexane to give 120 mg of 3-(1-methyl-3-indolyl)-4-(1-phenyl-3-indolyl)-1H-pyrrole-2,5-dione, m.p. 135°–137° C.

The furandione starting material was prepared as follows:

0.7 g of oxalyl chloride was added to a solution of 1.0 g of 1-phenylindole in 50 ml of dichloromethane at 0° C. After warming to room temperature and stirring for 16 hours the solvent was removed under reduced pressure. The obtained gum was treated with 50 ml of dichloromethane, 1.4 g of triethylamine and 1.0 g of 1-methylindol-3-ylacetic acid and the mixture was stirred for 4 hours. The solvent was evaporated and the residue was chromatographed on silica gel with ethyl acetate/hexane to give 190 mg of the furandione, m.p. 94°–96° C.

EXAMPLE 71

A solution of 50 mg of the product of Example 50 in 10 ml of DMF was treated with 4 ml of a 33% solution of methylamine in ethanol. The mixture was stirred for 16 hours and the solvents were then removed under reduced pressure. The residue was chromatographed on silica gel with ethyl acetate to give 46 mg of 3-[1-[3-(2-cyano-3-methylguanidino)propyl]-3-indolyl]-4-(1-methyl-3-indolyl)-1H-pyrrole-2,5-dione, m.p. 190°–193° C.

EXAMPLE 72

100 mg of the product of Example 50 were treated with 10 ml of ethanol, 10 ml of DMF and 20 ml of 40% aqueous diethylamine for 16 hours. The solvents were removed under reduced pressure and the residue was chromatographed on silica gel with 10% methanol in dichloromethane to give 53 mg of 3-[1-[3-(2-cyano-3,3-dimethylguanidino)propyl]-3-indolyl]-4-(1-methyl-3-indolyl)-1H-pyrrole-2,5-dione, m.p 150°–153° C.

EXAMPLE 73

A solution of 107 mg of the product of Example 67 in 30 ml of ethanol was treated with 10 mg of 10% Pd/C and shaken under 1 atmosphere of hydrogen for 16 hours. The solvent was removed under reduced pressure and the residue was chromatographed on silica gel with 1% to 10% methanol in dichloromethane. The product obtained was purified by dissolution in methanol, filtration, concentration of the filtrate, trituration of the residue with ethyl acetate, filtration and drying of the filter residue to give 22 mg of 3-[1-[3-(4-hydroxy-α-iminobenzylamino)propyl]-3-indolyl]-1H-pyrrole- 2,5-dione, m.p. >300° C.

EXAMPLE 74

150 mg of the product of Example 58 and 50 mg of 2-imidazolidinethione were heated together at reflux for 24 hours in 5 ml of ethanol. The solvent was evaporated and the residue was chromatographed on silica gel with 10 % to 25% methanol in dichloromethane to give 50 mg of 3-[1-[3-(2-imidazolin-2-ylthio)propyl]-3-indolyl]-4-(1-methyl-3-indolyl)-1H-pyrrole-2,5-dione methanesulphonate, m.p. 134°–136° C.

EXAMPLE 75

0.5 g of 3-[1-(3-aminopropyl)-3-indolyl]-4-(1-methyl-3-indolyl)-1H-pyrrole-2,5-dione acetate, 110 mg of sodium bicarbonate and 242 mg of 3,5-dimethyl-$N^2$-nitro-1-pyrazole-1-carboxamidine were heated together at reflux in 25 ml of ethanol for 4 hours. The solvent was removed under reduced pressure and the residue was chromatographed on silica gel with 1% to 5% methanol in dichloromethane to give 500 mg of 3-(1-methyl-3-indolyl)-4-[1-[3-(2-nitroguanidino)propyl]-3-indolyl]-1H-pyrrole-2,5-dione, m.p. 268°–270° C. (decomposition).

EXAMPLE 76

0.5 ml of pyridine and 115 mg of methanesulphonyl chloride were added to a solution of 50 mg of the product of Example 26a) in 35 ml of dichloromethane. The resulting solution was stirred overnight. 2 ml of pyridine were then added and the reaction mixture was heated to reflux for 8 hours. The cooled reaction mixture was washed with 2M hydrochloric acid, saturated sodium bicarbonate solution and water. The solution was dried and evaporated to give a solid which was recrystallized from dichloromethane/diethyl ether/hexane. There were obtained 40 mg of 3-(1-methyl-3-indolyl)-4-[1-[3-(methylsulphonamido)propyl]-3-indolyl]-1H-pyrrole-2,5-dione, m.p. 135°–138° C.

EXAMPLE 77

3-[1-[3-(Benzenesulphonamido)propyl]-3-indolyl]-4-(1-methyl-3-indolyl)-1H-pyrrole-2,5-dione, m.p. 125°–128° C. was obtained in an analogous manner to that described in Example 76.

EXAMPLE 78

30 μl of benzoyl chloride were added to a solution of 50 mg of the product of Example 26a) in 40 ml of dichloromethane. 200 μl of pyridine were then added and the mixture was stirred for 5 hours. The mixture was then washed with 2M hydrochloric acid and with saturated sodium bicarbonate solution, dried and evaporated. Crystallization of the residue from ethyl acetate/petroleum ether gave 45 mg of 3-[1-(3-benzamidopropyl)-3-indolyl]-4-(1-methyl-3-indolyl)-1H-pyrrole-2,5-dione, m.p. 138°–140° C.

EXAMPLE 79

102 mg of acetic anhydride were added to a solution of 50 mg of the product of Example 26a) in 40 ml of dichloromethane. The resulting solution was stirred for 1 hour. The mixture was washed with 2M hydrochloric acid and saturated sodium bicarbonate solution, dried and evaporated. Crystallization of the residue from dichloromethane/hexane gave 45 mg of 3-[1-(3-acetamidopropyl)-3-indolyl]-4-(1-methyl-3-indolyl)-1H-pyrrole-2,5- dione, m.p. 132°–136° C.

EXAMPLE 80

A mixture of 300 mg of the product of Example 58 and 2 ml of a 33% solution of dimethylamine in ethanol was heated at 90° C. for 1 hour. The mixture was evaporated, the residue was dissolved in 50 ml of ethyl acetate, the solution was washed with saturated sodium bicarbonate solution and treated with 10 ml of hydrochloric acid in ethyl acetate. The solvent was evaporated and the residue was purified on silica gel with dichloromethane/methanol/acetic acid/water (60:18:2:3). Crystallization from methanol/ethyl acetate yielded 40 mg of 3-[1-(3-(dimethylamino)propyl]-3-indolyl]-4-(1-methyl-3-indolyl)-1H-pyrrole-2,5-dione hydrochloride, m.p. 268°–270° C.

EXAMPLE 81

A mixture of 173 mg of the product of Example 58 and 2 ml of a 33% solution of trimethylamine in ethanol was heated at 90° C. for 3 hours. The solvent was evaporated and the residue was purified on silica gel with dichloromethane/methanol/acetic acid/water (60:18:2:3). Trituration with ethyl acetate gave 75 mg of trimethyl [3-[3-[3-(1-methyl-3-indolyl)-2,5-dioxo-3-pyrrolin-4-yl]-1-indolyl]propyl] ammonium methylsulphonate, m.p. 180°–185° C.

EXAMPLE 82

A solution of 500 mg of 3-[1-[3-[(t-butoxycarbonyl)(methyl)amino]propyl]-3-indolyl]-4-(1-methyl-3-indolyl) furan-2,5-dione in 1 ml of DMF and 2 ml of 33% aqueous ammonia was heated to 140° C. for 4 hours. The solvent was evaporated and the residue was taken up in 30 ml of ethyl acetate. The insoluble material was filtered off and a saturated solution of hydrogen chloride in ethyl acetate was added to the filtrate. The solvent was evaporated and the residue was chromatographed on silica gel with dichloromethane/methanol/acetic acid/water (60:18:2:3). Crystallization from methanol/ethyl acetate gave 75 mg of 3-(1-methyl-3-indolyl)-4-[1-[3-(methylamino)propyl]-3-indolyl]-1H-pyrrole-2,5-dione hydrochloride, m.p. 273°–275° C.

The furandione starting material was prepared as follows:

a) 3 g of 1-(3-bromopropyl)indole were treated with a 33% solution of methylamine in ethanol. The resulting solution was stirred for 6 hours. The solvent was evaporated and the residue was dissolved in 50 ml of dichloromethane and washed with a saturated sodium bicarbonate solution. The organic phase was dried and evaporated to give 2.30 g of 1-(3-methylaminopropyl)indole.

b) 2.67 g of di(t-butyl)dicarbonate and 1.24 g of triethylamine were added to a solution of 2.3 g of 1-(3-methylaminopropyl)indole in 40 ml of dichloromethane at 0° C. After 4 hours the mixture was washed with a saturated sodium bicarbonate solution, dried and evaporated to give 3.68 g of 1-[3-[(t-butoxycarbonyl)(methyl)amino]propyl] indole.

c) 1.14 ml of oxalyl chloride were added to a solution of 3.6 g of the product of b) in 40 ml of diethyl ether at 0° C. The resulting solution was stirred at 0° C. for 1 hour and the solvent was then evaporated. The residue was dissolved in 120 ml of dichloromethane and treated with 3.44 ml of triethylamine and 2.36 g of 1-methylindol-3-ylacetic acid. After stirring at room temperature for 18 hours the solvent was evaporated and the residue was purified on silica gel with ethyl acetate/petroleum ether (1:2). Evaporation of the solvents gave 1.4 g of the desired furandione, m.p 73°–80° C.

EXAMPLE 83

75 mg of methanesulphonyl chloride were added to a solution of 170 mg of the product of Example 21 in 8 ml of pyridine. The resulting solution was stirred for 4 hours and the solvent was then evaporated. The residue was purified on silica gel with ethyl acetate/petroleum ether (1:1). Recrystallization from ethyl acetate/hexane gave 40 mg of 3-[1-(3-chloropropyl)-3-indolyl]-4-(1-methyl-3-indolyl)-1H-pyrrole-2,5-dione, m.p. 254°–256° C.

EXAMPLE 84

In an analogous manner to that described in Example 26 there were manufactured:

3-[1-(2-Aminoethyl)-3-indolyl]-4-(1-methyl-3-indolyl)-1H-pyrrole-2,5-dione hydrochloride, m.p. 245°–247° C.;

3-[1-(4-aminobutyl)-3-indolyl]-4-(1-methyl-3-indolyl)-1H-pyrrole-2,5-dione hydrochloride, m.p. 190°–192° C.; and 3-[1-(5-aminopentyl)-3-indolyl]-4-(1-methyl-3-indolyl)-1H-pyrrole-2,5-dione, m.p. 180°–182° C.

EXAMPLE 85

A solution of 1.6 g of 3-[1-(2-acetoxyethyl)-3-indolyl]-4-(1-methyl-3-indolyl)furan-2,5-dione in 4 ml of DMF and 8 ml of 33% aqueous ammonia was heated to 160° C. for 4 hours. The precipitate was filtered off and dried to give 1.04 g of 3-[1-(2-hydroxyethyl)-3-indolyl]-4-(1-methyl-3-indolyl)-1H-pyrrole-2,5-dione, m.p. 250°–252° C.

The furandione starting material was prepared as follows:

a) 11.7 g of indole in 500 ml of DMF were treated with 4 g of sodium hydride dispersed in mineral oil. After 1 hour the mixture was cooled in an ice bath and 10 ml of ethylene oxide were added. The mixture was allowed to warm to room temperature and was then stirred for 2 hours. The solvent was evaporated and the residue was treated with 50 ml of water and neutralized with 2M hydrochloric acid. The product was extracted into dichloromethane, the solvent was evaporated and the residue was chromatographed with ethyl acetate/petroleum ether to give 7.6 g of 1-(2-hydroxyethyl) indole.

b) An ice-cooled solution of 4.6 g of 1-(2-hydroxyethyl) indole in 10 ml of diethyl ether was treated with 1 ml of pyridine and 4 ml of acetic anhydride. After 2 hours 50 ml of water were added, the mixture was extracted with 100 ml of dichloromethane and the dichloromethane extract was dried. The solvent was evaporated to give 5.7 g of 1-(2-acetoxyethyl)indole.

c) 2.57 ml of oxalyl chloride were added to a solution of 5.7 g of 1-(2-acetoxyethyl)indole in 70 ml of dichloromethane at 0° C. The resulting solution was stirred for 2 hours and the solvent was then evaporated. To the residue, dissolved in 210 ml of dichloromethane, were added 7.7 ml of triethylamine and 5.29 g of 1-methylindole-3-acetic acid under a nitrogen atmosphere. After stirring for 18 hours the solvent was evaporated and the residue was purified on silica gel with ethyl acetate/petroleum ether (1:2). Crystallization from ethyl acetate/hexane gave 1.87 g of 3-[1-(2-acetoxyethyl)-3-indolyl]-4-(1-methyl-3-indolyl)furan-2,5-dione, m.p. 198°–199° C.

EXAMPLE 86

200 mg of 3-(1-methyl-3-indolyl)-4-(4-pyridyl)furan-2,5-dione were treated with 5 ml of DMF and 5 ml of 33% aqueous ammonia. The resulting solution was heated at 140° C. for 17 hours. After cooling, the suspension was diluted with water. The product was filtered off, washed with water and dried to give 144 mg of 3-(1-methyl-3-indolyl)-4-(4-pyridyl)-1H-pyrrole-2,5-dione, m.p. 332°–334° C.

The furandione starting material was prepared as follows:

5 g of 4-pyridyl-acetic acid hydrochloride and 3.72 g of diisopropylethylamine in 50 ml of dichloromethane were treated at 0° C. firstly with 6.37 g of 1-methylindole-3-glyoxylyl chloride in 50 ml of dichloromethane and then with 7.5 g of diisopropylethylamine. The mixture was allowed to warm to room temperature and was then stirred for 65 hours. The solvent was removed under reduced pressure and the residue was taken up in dichloromethane and chromatographed on silica gel with ethyl acetate. The product-containing fractions were concentrated. Crystallization from ethyl acetate/hexane yielded 940 mg of 3-(1-methyl-3-indolyl)-4-(4-pyridyl)furan-2,5-dione, m.p. 217°–219° C.

EXAMPLE 87

In an analogous manner to that described in Example 86 there were manufactured:

3-(1-Methyl-3-indolyl)-4-(3-pyridyl)-1H-pyrrole-2,5-dione, m.p. 278°–279° C.; and 3-(1-methyl-3-indolyl)-4-(2-pyridyl)-1H-pyrrole-2,5-dione, m.p. 242°–244° C.

EXAMPLE 88

135 mg of 3-(1-methyl-3-indolyl)-4-(3-pyrrolyl)furan-2,5-dione were treated with 5 ml of DMF and 5 ml of 33% aqueous ammonia. The solution was heated at 140° C. for 4 hours. The cooled solution was diluted with water and extracted with dichloromethane. The dichloromethane extracts were dried and concentrated. Chromatography of the residue on silica gel with ethyl acetate/hexane (1:1) followed by crystallization from ethyl acetate/hexane gave 50 mg of 3-(1-methyl-3-indolyl)-4-(3-pyrrolyl)-1H-pyrrole-2,5-dione, m.p. 240°–241° C.

The furandione starting material was prepared as follows:

a) 1 g of 1-(benzenesulphonyl)-3-pyrrolylacetic acid in 25 ml of dichloromethane was treated at 0° C. with a solution of 837 mg of 1-methylindole-3-glyoxylyl chloride in 25 ml of dichloromethane and then with 975 mg of diisopropylethylamine. The mixture was allowed to warm to room temperature and was then stirred for 22 hours. After concentration and chromatography of the residue on silica gel with ethyl acetate/hexane (1:1) there were obtained 540 mg of 3-[1-(benzenesulphonyl)-3-pyrrolyl]-4-(1-methyl-3-indolyl)furan-2,5-dione.

b) 255 mg of the product of a) in 10 ml of ethanol were treated with 2.5 ml of 2.5M aqueous sodium hydroxide. The solution was left to stand at room temperature for 17 hours. After dilution with 10 ml of water the mixture was extracted with diethyl ether. The aqueous solution was acidified with concentrated hydrochloric acid and extracted with ethyl acetate. The ethyl acetate extracts were dried and concentrated to give 140 mg of the desired furandione, m/e 292 ($M^+$).

EXAMPLE 89

1.455 g of the product of Example 58 in 45 ml of ethanol were treated with 364 mg of thiourea and the mixture was heated at reflux for 18 hours. After cooling the precipitate was filtered off and washed with ethanol and with diethyl ether. The solid was dried to give 1.33 g of 3-[1-[3-(amidinothio)propyl]-3-indolyl]-4-(1-methyl-3-indolyl)-1H-pyrrole-2,5-dione methanesulphonate, m.p. 236°–238° C. (decomposition).

EXAMPLE 90

In an analogous manner to that described in Example 89 there were manufactured:

3-[1-[2-(Amidinothio)ethyl]-3-indolyl]-4-(1-methyl-3-indolyl)-1H-pyrrole-2,5-dione methanesulphonate, m.p. 238°–240° C. (decomposition);

3-[1-[4-(amidinothio)butyl]-3-indolyl]-4-(1-methyl-3-indolyl)-1H-pyrrole-2,5-dione methanesulphonate, m.p. 150° C. (decomposition); and 3-[1-[5-(amidinothio)pentyl]-3-indolyl]-4-(1-methyl-3-indolyl)-1H-pyrrole-2,5-dione methanesulphonate, m.p. 130° C. (decomposition).

EXAMPLE 91

450 mg of the product of Example 58 in 20 ml of DMSO were treated with 116 mg of sodium cyanide. The mixture was heated at 50° C. for 8 hours, then cooled and poured into water. The mixture was extracted with ethyl acetate and the extracts were dried. Concentration and chromatography on silica gel with toluene/ acetic acid (9:1) gave a solid which was triturated with diethyl ether, filtered off and dried. There were obtained 69 mg of 3-[1-(3-cyanopropyl)-3-indolyl]-4-(1-methyl-3-indolyl)-1H-pyrrole-2,5-dione, m.p. 245°–247° C.

EXAMPLE 92

3-[1-(4-Cyanobutyl)-3-indolyl]-4-(1-methyl-3-indolyl)-1H-pyrrole-2,5-dione, m.p. 195°–198° C. was manufactured in an analogous manner to that described in Example 91.

EXAMPLE 93

100 mg of the product of Example 91 in 20 ml of ethanol were treated with hydrogen chloride gas until a saturated solution was obtained. After 6 hours the solvent was evaporated and the residue was dissolved in 50 ml of ethanol. The solution was cooled to 0° C., saturated with ammonia gas and then allowed to warm to room temperature. After standing for 17 hours the solvent was evaporated. The residue was dissolved in water and extracted with ethyl acetate. The aqueous solution was lyophilized to give 84 mg of 3-[1-(3-amidinopropyl)-3-indolyl]-4-(1-methyl-3-indolyl)-1H-pyrrole-2,5-dione hydrochloride, m.p. 175°–177° C.

EXAMPLE 94

100 mg of the product of Example 58 in 10 ml of DMSO were treated with 120 mg of 5-mercapto-1-methyltetrazole sodium salt. The solution was heated at 55° C. for 6 hours, then cooled and poured into water. The aqueous phase was extracted with ethyl acetate. The ethyl acetate extracts were dried and concentrated. Chromatography on silica gel with dichloromethane/ethyl acetate (4:1) gave 48 mg of 3-(1-methyl-3-indolyl)-4-[1-[3-(1-methyl-5-tetrazolylthio)propyl]-3-indolyl]-1H-pyrrole-2,5-dione, m.p. 95°–97° C.

EXAMPLE 95

600 mg of the product of Example 21 in 60 ml of dichloromethane were treated with 237 mg of pyridine. The mixture was added at 5°–10° C. to a solution of 855 mg of trifluoromethanesulphonic anhydride in 15 ml of dichloromethane. After 1 hour at 5°–10° C. the mixture was added to 944 mg of 1,2-diaminoethane in 20 ml of dichloromethane. The mixture was stirred at room temperature for 15 minutes and then washed with a sodium bicarbonate solution. The dichloromethane solution was dried and concentrated. Chromatography of the residue on silica gel with chloroform/methanol/acetic acid/water (60:18:2:3) gave a gum which was dissolved in 50 ml of ethanol. The solution was treated with 25 ml of 1M hydrochloric acid and concentrated. The residue was triturated with diethyl ether, filtered off and dried to give 221 mg of 3-[1-[3-(2-aminoethylamino)propyl]-3-indolyl]-4-(1-methyl-3-indolyl)-1H-pyrrole-2,5-dione, m.p. 190°–193° C.

EXAMPLE 96

100 mg of the product of Example 58 in 5 ml of DMSO were treated with 30 mg of sodium methanethiolate. The solution was stirred for 30 minutes and then diluted with water. The precipitate was filtered off, washed with water and dried to give 52 mg of 3-(1-methyl-3-indolyl)-4-[1-[3-(methylthio)propyl]-3-indolyl]-1H-pyrrole-2,5-dione, m.p. 222°–224° C.

EXAMPLE 97

116 mg of the product of Example 96 in 5 ml of dichloromethane were treated at 0° C. with 60 mg of 85% metachloroperbenzoic acid in 5 ml of dichloromethane. The solution was allowed to warm to room temperature and was then stirred for 1 hour. The solution was washed with aqueous sodium bicarbonate and dried. The solution was concentrated and the residue was crystallized from ethyl acetate/hexane to give 84 mg of rac-3-(1-methyl-3-indolyl)-4-[1-(3-methylsulphinylpropyl)-3-indolyl]-1H-pyrrole-2,5-dione, m.p. 140° C.

EXAMPLE 98

90 mg of the product of Example 97 in 5 ml of dichloromethane were treated with 60 mg of 85% metachloroperbenzoic acid in 5 ml of dichloromethane. The solution was stirred for 2 hours and then washed with aqueous sodium bicarbonate. The solution was dried and concentrated. Chromatography of the residue on silica gel with dichloromethane/ethyl acetate (1:1) and recrystallization from ethyl acetate/hexane gave 25 mg of 3-(1-methyl-3-indolyl)-4-[1-(3-methylsulphonylpropyl)-3-indolyl]-1H-pyrrole-2,5-dione, m.p. 225°–227° C.

EXAMPLE 99

838 mg of the product of Example 58 in 15 ml of DMSO were treated with 600 mg of potassium thiolacetate. The solution was stirred for 3 hours and then diluted with water. The solution was extracted with ethyl acetate and the ethyl acetate extracts were dried. Concentration and chromatography on silica gel with ethyl acetate gave 723 mg of 3-[1-[3-(acetylthio)propyl]-3-indolyl]-4-(1-methyl-3-indolyl)-1H-pyrrole-2,5-dione, m.p. 210°–213° C.

EXAMPLE 100

350 mg of the product of Example 99 in 20 ml of 50% methanol/DMF were treated with 0.5 ml of 33% aqueous ammonia. The mixture was stirred for 17 hours, then diluted with 20 ml of sodium chloride solution and extracted with ethyl acetate. The ethyl acetate extracts were dried and evaporated. Chromatography of the residue on silica gel with ethyl acetate/hexane (3:1) gave 266 mg of 3-[-1-(3-mercaptopropyl)-3-indolyl]-4-(1-methyl-3-indolyl)-1H-pyrrole-2,5-dione, m.p. 155°–157° C.

EXAMPLE 101

0.71 g of trifluoromethanesulphonic anhydride was added to a solution of 0.5 g of the product of Example 21 in 10 ml of pyridine at 0° C. The mixture was stirred at room temperature for 3 days and then evaporated. The residue was chromatographed on silica gel with 10% methanol in dichloromethane to give 0.11 g of 3-(1-methyl-3-indolyl)-4-[1-[3-(1-pyridinio)propyl]-3-indolyl]-1H-pyrrole-2,5-dione trifluoromethanesulphonate, m.p. 87°–88° C.

EXAMPLE 102

Chromatography of the free base of Example 26a) on silica gel with dichloromethane/methanol/acetic acid/water (60:18:2:3) gave the corresponding acetate utilized as starting material in Example 64, 66 and 75.

The following Examples illustrate typical pharmaceutical preparations containing compounds provided by the present invention:

Tablets and capsules containing the following ingredients may be produced in a conventional manner:

| Example A | |
|---|---|
| Ingredient | Per tablet |
| Compound of formula I | 5.0 mg |
| Lactose | 125.0 mg |
| Maize starch | 75.0 mg |
| Talc | 4.0 mg |
| Magnesium stearate | 1.0 mg |
| Tablet weight | 210.0 mg |

| Example B | |
|---|---|
| Ingredient | Per capsule |
| Compound of formula I | 10.0 mg |
| Lactose | 165.0 mg |
| Maize starch | 20.0 mg |
| Talc | 5.0 mg |
| Capsule fill weight | 200.0 mg |

We claim:

1. A compound of the formula

I

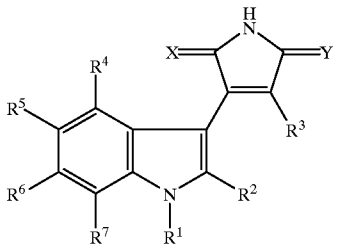

wherein $R^1$ signifies hydrogen, alkyl, aryl, aralkyl, alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula (a)

$$-(CH_2)_n-W-Het,$$

(b)

$$-(CH)_n-T-\overset{V}{\overset{\|}{C}}-Z$$

-continued (c)

$$-(CH_2)_n-NH-\overset{O}{\overset{\|}{C}}-Im \quad \text{or}$$

(d)

$$-(CH_2)_n-NH-\overset{NH}{\overset{\|}{C}}-Ar$$

in which

Het signifies a heterocyclyl group,

W signifies NH, S or a bond,

T signifies NH or S

V signifies O, S, NH. $NNO_2$, NCN or $CHNO_2$,

Z signifies alkylthio, amino, monoalkylamino or dialkylamino,

Im signifies 1-imidazolyl,

Ar signifies aryl, and n stands for 2–6;

$R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl;

$R^3$ signifies a carbocyclic or heterocyclic aromatic group;

$R^4$, $R^5$, $R^6$ and $R^7$ each independently signify hydrogen, halogen, alkyl, hydroxy, alkoxy, aryloxy, haloalkyl, nitro, amino, acylamino, monoalkylamino, dialkylamino, alkylthio, alkylsulphinyl or alkylsulphonyl;

and one of X and Y signifies O and the other signifies O, S, (H,OH) or (H,H);

with the proviso that $R^1$ has a significance different from hydrogen when $R^2$ signifies hydrogen, $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; or a pharmaceutically acceptable salt of acidic compounds of formula I with bases and of basic compounds of formula I with acids.

2. A compound according to claim 1, wherein $R^1$ signifies hydrogen, alkyl, aralkyl, alkoxyalkyl, hydroxyalkyl, haloalkyl, aminoalkyl, monoalkylaminoalkyl, dialkylaminoalkyl, azidoalkyl, acylaminoalkyl, alkylsulphonylaminoalkyl, arylsulphonylaminoalkyl, mercaptoalkyl, alkylthioalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl.

3. A compound according to claim 2, wherein $R^1$ signifies alkyl or aminoalkyl.

4. A compound according to claim 1, wherein $R^1$ signifies isothiocyanatoalkyl or a group of formula (b) in which T signifies S, V signifies NH and Z signifies amino or in which T signifies NH, V signifies NH or $NNO_2$ and Z signifies amino.

5. A compound according to claim 4, wherein $R^2$ signifies hydrogen.

6. A compound according to claim 5, wherein $R^3$ signifies phenyl which is monosubstituted by halogen, alkyl, alkoxy, haloalkyl, nitro, amino, alkylthio, alkylsulphinyl or alkylsulphonyl.

7. A compound according to claim 5, wherein $R^3$ signifies a group of the formula (I)

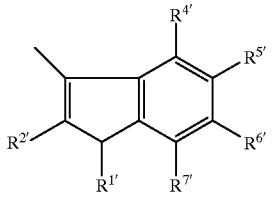

wherein $R^{1'}$, $R^{2'}$, $R^{4'}$, $R^{5'}$, $R^{6'}$ and $R^{7'}$ have any of the values accorded to $R^1$, $R^2$, $R^4$, $R^5$, $R^6$ and $R^7$ in claim 1.

8. A compound according to claim 7, wherein $R^4$, $R^5$, $R^6$ and $R^7$ each signify hydrogen.

9. A compound according to claim 8, wherein $R^1$ signifies methyl, 3-aminopropyl, 3-isothio-cyanatopropyl or a group of formula (b) in which T signifies S, V signifies NH, Z signifies amino and n stands for 3 or in which T signifies NH, V signifies NH or $NNO_2$, Z signifies amino and n stands for 3, $R^2$ signifies hydrogen, $R^3$ signifies phenyl which is mono-substituted by chlorine, bromine, methyl, methoxy, trifluoromethyl, nitro, amino, methylsulphinyl or methylsulphonyl or a group of formula (i) given in claim 7 in which $R^{1'}$ signifies methyl and $R^{2'}$, $R^{4'}$, $R^{5'}$, $R^{6'}$ and $R^{7'}$ each signify hydrogen, and $R^4$, $R^5$, $R^6$ and $R^7$ each signify hydrogen.

10. A compound in accordance with claim 1 selected from the group consisting of:

3-(2-Chlorophenyl)-4-(1-methyl-3-indolyl)-1H-pyrrole-2,5-dione, 3-(2-Nitrophenyl)-4-(1-methyl-3-indolyl)-1H-pyrrole-2,5-dione, 3,4-Bis(1-methyl-3-indolyl)-1H-pyrrole-2,5-dione, 3-[1-(3-Aminopropyl)-3-indolyl]-4-(1-methyl-3-indolyl)-1H-pyrrole-2,5-dione 1-[1-[3-(Amidinothio)propyl]-3-indolyl]-4-(1-methyl-3-indolyl)-1H-pyrrole-2,5-dione, 3-(1-Methyl-3-indolyl)-4-[1-[3-(2-nitroguanidino)propyl]-3-indolyl]-1H-pyrrole-2,5-dione and 3-[1-(3-Isothiocyanatopropyl)-3-indolyl]-4-(1-methyl-3-indolyl)-1H-pyrrole-2,5-dione.

11. A pharmaceutical composition comprising an effective amount of a compound of the formula

I

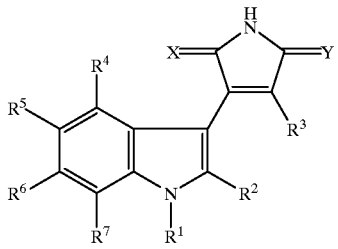

wherein $R^1$ signifies hydrogen, alkyl, aryl, aralkyl, alkoxyalkyl, hydroxyalkyl, haloalkyl, aminoalkyl, monoalkylaminoalkyl, dialkylaminoalkyl, trialkylaminoalkyl, aminoalkylaminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula (a)

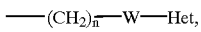

(b)

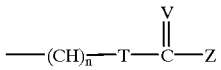

(c)

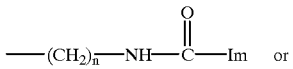

or (d)

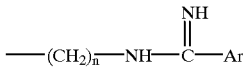

in which

Het signifies a heterocyclyl group,

W signifies NH, S or a bond,

T signifies NH or S,

V signifies O, S, NH, $NNO_2$, NCN or $CHNO_2$,

Z signifies alkylthio, amino, monoalkylamino or dialkylamino,

Im signifies 1-imidazolyl,

Ar signifies aryl, and n stands for 2–6;

$R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl;

$R^3$ signifies a carbocyclic or heterocyclic aromatic group;

$R^4$, $R^5$, $R^6$ and $R^7$ each independently signify hydrogen, halogen, alkyl, hydroxy, alkoxy, aryloxy, haloalkyl, nitro, amino, acylamino, monoalkylamino, dialkylamino, alkylthio, alkylsulphinyl or alkylsulphonyl;

and one of X and Y signifies O and the other signifies O, S, (H,OH) or (H,H);

with the proviso that $R^1$ has a significance different from hydrogen when $R^2$ signifies hydrogen, $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; or a pharmaceutically acceptable salt of acidic compounds of formula I with bases and of basic compounds of formula I with acids, and an inert carrier material.

12. A pharmaceutical composition in accordance with claim 11, wherein the compound of formula I is selected from the group consisting of:

3-(2-Chlorophenyl)-4-(1-methyl-3-indolyl)-1H-pyrrole-2,5-dione, 3-(2-Nitrophenyl)-4-(1-methyl-3-indolyl)-1H-pyrrole-2,5-dione, 3,4-Bis(1-methyl-3-indolyl)-1H-pyrrole-2,5-dione, 3-[1-(3-Aminopropyl)-3-indolyl]-4-(1-methyl-3-indolyl)-1H-pyrrole-2,5-dione 1-[1-[3-(Amidinothio)propyl]-3-indolyl]-4-(1-methyl-3-indolyl)-1H-pyrrole-2,5-dione, 3-(1-Methyl-3-indolyl)-4-[1-[3-(2-nitroguanidino)propyl]-3-indolyl]-1H-pyrrole-2,5-dione, and 3-[1-(3-Isothiocyanatopropyl)-3-indolyl]-4-(1-methyl-3-indolyl)-1H-pyrrole-2,5-dione.

*13. A compound of the formula, 3-(1-*methyl*-3-indolyl)-4-(1-methyl-6-nitro-3-indolyl)-1H-pyrrole-2,5-dione.*

*14. A pharmaceutical composition, comprising an effective amount of 3-(1-methyl-3-indolyl)-4-(1-methyl-6-nitro-3-indolyl)-1H-pyrrole-2,5-dione and an inert carrier material.*

* * * * *